United States Patent [19]
Lucas et al.

[11] Patent Number: 5,997,872
[45] Date of Patent: Dec. 7, 1999

[54] ISOLATED NUCLEIC ACID MOLECULE CODING FOR TUMOR REJECTION ANTIGEN PRECURSOR MAGE-C1 AND USES THEREOF

[75] Inventors: Sophie Lucas; Charles De Smet; Thierry Boon-Falleur, all of Brussels, Belgium

[73] Assignee: Ludwig Institute for Cancer Research, New York, N.Y.

[21] Appl. No.: 08/993,118

[22] Filed: Dec. 17, 1997

Related U.S. Application Data

[62] Division of application No. 08/845,528, Apr. 25, 1997.

[51] Int. Cl.[6] .......................... A61K 39/00; A61K 38/00; C07H 21/04; G01N 33/574
[52] U.S. Cl. .......................... 424/185.1; 514/12; 530/324; 536/23.5; 435/7.23
[58] Field of Search ........................ 424/185.1; 435/7.23; 514/12; 530/324; 536/23.5

*Primary Examiner*—Sheela Huff
*Assistant Examiner*—Yvonne Eyler
*Attorney, Agent, or Firm*—Fulbright & Jaworski, LLP.

[57] ABSTRACT

The invention relates to an isolated DNA sequence which codes for an antigen expressed by tumor cells which maybe recognized by cytotoxic T cells, leading to lysis of the tumor cells which express it. This invention also relates to vectors which are designed to encode the antigen expressed by tumor cells and also to cells transfected by the DNA sequence or vectors which comprise the DNA sequence. Various therapeutic and diagnostic uses arising out of the properties of the DNA and the antigen for which it codes are also part of this invention.

2 Claims, 13 Drawing Sheets

Figure 1(A)

| | |
|---|---|
| G*GATC*GTCTCAGGTCAG<u>CGGAGGGA</u> | 25 |
| <span style="padding-left:5em;">SL33</span> | |
| <u>GGAGACTTA</u>TAGACCTATCCAGTCT | 50 |
| TCAAGGTGCTCCAGAAAGCAGGAGT | 75 |
| TGAAGACCTGGGTGTGAGGGACACA | 100 |
| TACATCCTAAAAGCACCACAGCAGA | 125 |
| GGAGGCCCAGGCAGTGCCAGGAGTC | 150 |
| AAGGTTCCCAGAAGACAAACCCCCT | 175 |
| AGGAAGACAGGCGACCTGTGAGGCC | 200 |
| <u>CTAGAGCACCACCTTAA</u>GAGAAGAA | 225 |
| <span style="padding-left:3em;">SL34</span> | |
| GAGCTGTAAGCCGGCCTTTGTCAGA | 250 |
| GCCATCATGGGGGACAAGGATATGC | 275 |
| CTACTGCTGGGATGCCGAGTCTTCT | 300 |
| CCAGAGTTCCTCTGAGAGTCCTCAG | 325 |
| AGTTGTCCTGAGGGGGAGGACTCCC | 350 |
| AGTCTCCTCTCCAGATTCCCCAGAG | 375 |
| TTCTCCTGAGAGCGACGACACCCTG | 400 |
| TATCCTCTCCAGAGTCCTCAGAGTC | 425 |
| GTTCTGAGGGGGAGGACTCCTCGGA | 450 |
| TCCTCTCCAGAGACCTCCTGAGGGG | 475 |
| AAGGACTCCCAGTCTCCTCTCCAGA | 500 |
| TTCCCCAGAGTTCTCCTGAGGGCGA | 525 |
| CGACACCCAGTCTCCTCTCCAGAAT | 550 |
| TCTCAGAGTTCTCCTGAGGGGAAGG | 575 |
| ACTCCCTGTCTCCTCTAGAGATTTC | 600 |
| TCAGAGCCCTCCTGAGGGTGAGGAT | 625 |
| GTCCAGTCTCCTCTGCAGAATCCTG | 650 |
| CGAGTTCCTTCTTCTCCTCTGCTTT | 675 |
| ATTGAGTATTTTCCAGAGTTCCCCT | 700 |

Figure 1(B)

| | |
|---|---|
| GAGAGAACTCAGAGTACTTTTGAGG | 725 |
| GTTTTCCCCAGTCTCCTCTCCAGAT | 750 |
| TCCTGTGAGCTCCTCCTCCTCCTCC | 775 |
| ACTTTATTGAGTCTTTTCCAGAGTT | 800 |
| CCCCTGAGAGAACTCAGAGTACTTT | 825 |
| TGAGGGTTTTCCCCAGTCTCTTCTC | 850 |
| CAGATTCCTATGACCTCCTCCTTCT | 875 |
| CCTCTACTTTATTGAGTATTTTCCA | 900 |
| GAGTTCTCCTGAGAGTGCTCAAAGT | 925 |
| ACTTTTGAGGGTTTTCCCCAGTCTC | 950 |
| CTCTCCAGATTCCTGGGAGCCCCTC | 975 |
| CTTCTCCTCCACTTTACTGAGTCTT | 1000 |
| TTCCAGAGTTCCCCTGAGAGAACTC | 1025 |
| ACAGTACTTTTGAGGGTTTTCCCCA | 1050 |
| GTCTCCTCTCCAGATTCCTATGACC | 1075 |
| TCCTCCTTCTCCTCTACTTTATTGA | 1100 |
| GTATTTTCCAGAGTTCTCCTGAGAG | 1125 |
| TGCTCAAAGTACTTTTGAGGGTTTT | 1150 |
| CCCCAGTCTCCTCTCCAGATTCCTG | 1175 |
| GGAGCCCCTCCTTCTCCTCCACTTT | 1200 |
| ACTGAGTCTTTTCCAGAGTTCCCCT | 1225 |
| GAGAGAACTCACAGTACTTTTGAGG | 1250 |
| GTTTTCCCCAGTCTCCTCTCCAGAT | 1275 |
| TCCTATGACCTCCTCCTTCTCCTCT | 1300 |
| ACTTTATTGAGTATTTTACAGAGTT | 1325 |
| CTCCTGAGAGTGCTCAAAGTGCTTT | 1350 |
| TGAGGGTTTTCCCCAGTCTCCTCTC | 1375 |
| CAGATTCCTGTGAGCTCCTCTTTCT | 1400 |

Figure 1(C)

| Sequence | Position |
|---|---|
| CCTACACTTTATTGAGTCTTTTCCA | 1425 |
| GAGTTCCCCTGAGAGAACTCAGAGT | 1450 |
| ACTTTTGAGGGTTTTCCCCAGTCTC | 1475 |
| CTCTCCAGATTCCTGTGAGCTCCTC | 1500 |
| CTCCTCCTCCTCCACTTTATTGAGT | 1525 |
| CTTTTCCAGAGTTCCCTGAGTGTA | 1550 |
| CTCAAGTACTTTTGAGGGTTTTCC | 1575 |
| CCAGTCTCCTCTCCAGATTCCTCAG | 1600 |
| AGTCCTCCTGAAGGGGAGAATACCC | 1625 |
| ATTCTCCTCTCCAGATTGTTCCAAG | 1650 |
| TCTTCCTGAGTGGGAGGACTCCCTG | 1675 |
| TCTCCTCACTACTTTCCTCAGAGCC | 1700 |
| CTCCTCAGGGGGAGGACTCCCTATC | 1725 |
| TCCTCACTACTTTCCTCAGAGCCCT | 1750 |
| CCTCAGGGGGAGGACTCCCTGTCTC | 1775 |
| CTCACTACTTTCCTCAGAGCCCTCA | 1800 |
| GGGGGAGGACTCCCTGTCTCCTCAC | 1825 |
| TACTTTCCTCAGAGCCCTCCTCAGG | 1850 |
| GGGAGGACTCCATGTCTCCTCTCTA | 1875 |
| CTTTCCTCAGAGTCCTCTTCAGGGG | 1900 |
| GAGGAATTCCAGTCTTCTCTCCAGA | 1925 |
| GCCCTGTGAGCATCTGCTCCTCCTC | 1950 |
| CACTCCATCCAGTCTTCCCCAGAGT | 1975 |
| TTCCCTGAGAGTTCTCAGAGTCCTC | 2000 |
| CTGAGGGCCTGTCCAGTCTCCTCT | 2025 |
| CCATAGTCCTCAGAGCCCTCCTGAG | 2050 |
| GGGATGCACTCCAATCTCCTCTCC | 2075 |
| AGAGTCCTGAGAGTGCTCCTGAGGG | 2100 |

Figure 1(D)

| | |
|---|---|
| GGAGGATTCCCTGTCTCCTCTCCAA | 2125 |
| ATTCCTCAGAGTCCTCTTGAGGGAG | 2150 |
| AGGACTCCCTGTCTTCTCTCCATTT | 2175 |
| TCCTCAGAGTCCTCCTGAGTGGGAG | 2200 |
| GACTCCCTCTCTCCTCTCCACTTTC | 2225 |
| CTCAGTTCCTCCTCAGGGGGAGGA | 2250 |
| CTTCCAGTCTTCTCTCCAGAGTCCT | 2275 |
| GTGAGTATCTGCTCCTCCTCCACTT | 2300 |
| CTTTGAGTCTTCCCCAGAGTTTCCC | 2325 |
| TGAGAGTCCTCAGAGTCCTCCTGAG | 2350 |
| GGGCCTGCTCAGTCTCCTCTCCAGA | 2375 |
| GACCTGTCAGCTCCTTCTTCTCCTA | 2400 |
| CACTTTAGCGAGTCTTCTCCAAAGT | 2425 |
| TCCCATGAGAGTCCTCAGAGTCCTC | 2450 |
| CTGAGGGGCCTGCCCAGTCTCCTCT | 2475 |
| CCAGAGTCCTGTGAGCTCCTTCCCC | 2500 |
| TCCTCCACTTCATCGAGTCTTTCCC | 2525 |
| AGAGTTCTCCTGTGAGCTCCTTCCC | 2550 |
| CTCCTCCACTTCATCGAGTCTTTCC | 2575 |
| AAGAGTTCCCTGAGAGTCCTCTCC | 2600 |
| AGAGTCCTGTGATCTCCTTCTCCTC | 2625 |
| CTCCACTTCATTGAGCCCATTCAGT | 2650 |
| GAAGAGTCCAGCAGC<u>CCAGTAGATG</u> | 2675 |
| <span style="margin-left:2em">SL26</span> | |
| <u>AATATACAAGTT</u>CCTCAGACACCTT | 2700 |
| GCTAGAGAGTGATTCCTTGACAGAC | 2725 |
| AGCGAGTCCTTGATAGAGAGCGAGC | 2750 |
| CCTTGTTCACTTATACACTGGATGA | 2775 |
| AAAGGTGGACGAGTTGGCGCGGTTT | 2800 |

Figure 1(E)

| | |
|---|---|
| CTTCTCCTCAAATATC<u>AAGTGAAGC</u> | 2825 |
|     SL27 | |
| <u>AGCCTATCA</u>CAAAGGCAGAGATGCT | 2850 |
| GACGAATGTCATCAGCAGGTACACG | 2875 |
| GGCTACTTTCCTGTGATCTTCAGGA | 2900 |
| AAGCCCGTGAGTTCATAGAGATACT | 2925 |
| TTTTGGCATTTCCCTGAGAGAAGTG | 2950 |
| GACCCTGATGACTCCTATGTCTTTG | 2975 |
| TAAACACATTAGACCTCACCTCTGA | 3000 |
| GGGGTGTCTGAGTGATGAGCAGGGC | 3025 |
| ATGTCCCAGAACCGCCTCCTGATTC | 3050 |
| TTATTCTGAGTATCATCTTCATAAA | 3075 |
| GGGCACCTATGCCTCTGAGGAGGTC | 3100 |
| ATCTGGATGTGCTGAGTGGAATAG | 3125 |
| GGGTGCGTGCTGGGAGGGAGCACTT | 3150 |
| TGCCTTTGGGGAGCCCAGGGAGCTC | 3175 |
| CTCACTAAAGTTTGGGTGCAGGAAC | 3200 |
| ATTACCTAGAGTACCGGGAGGTGCC | 3225 |
| CAACTCTTCTCCTCCTCGTTACGAA | 3250 |
| TTCCTGTGGGGTCCAAGAGCTCATT | 3275 |
| CAGAAGTCATTAAGAGGAAAGTAGT | 3300 |
| AGAGTTTTGGCCATGCTAAAGAAT | 3325 |
| ACCGTCCCTATTACCTTTCCATCCT | 3350 |
| CTTACAAGGATGCTTTGAAAGATGT | 3375 |
| GGAAGAGAGAGCCCAGGCCATAATT | 3400 |
| GACACCACAGATGATTCGACTGCCA | 3425 |
| CAGAAAGTGCAAGCTCCAGTGTCAT | 3450 |
| GTCCCCAGCTTCTCTTCTGAGTGA | 3475 |
| AGTCTAGGGCAGATTCTTCCCTCTG | 3500 |

Figure 1(F)

| Sequence | Position |
|---|---|
| AGTTTGAAGGGGGCAGTCGAGTTTC | 3525 |
| TACGTGGTGGAGGGCCTGGTTGAGG | 3550 |
| CTGGAGAGAACACAGTGCTATTTGC | 3575 |
| ATTTCTGTTCCATATGGGTAGTTAT | 3600 |
| GGGGTTTACCTGTTTTACTTTTGGG | 3625 |
| TATTTTTCAAATGCTTTTCCTATTA | 3650 |
| ATAACAGGTTTAAATAGCTTCAGAA | 3675 |
| TCCTAGTTTATGCACATGAGTCGCA | 3700 |
| CATGTATTGCTGTTTTTCTGGTTTA | 3725 |
| AGAGTAACAGTTTGATATTTTGTAA | 3750 |
| AAACAAAACACACCCAAACACACC | 3775 |
| ACATTGGGAAAACCTTCTGCCTCAT | 3800 |
| TTTGTGATGTGTCACAGGTTAATGT | 3825 |
| GGTGTTACTGTAGGAATTTTCTTGA | 3850 |
| AACTGTGAAGGAACTCTGCAGTTAA | 3875 |
| ATAGTGGAATAAAGTAAAGGATTGT | 3900 |
| TAATGTTTGCATTTCCTCAGGTCCT | 3925 |
| TTAGTCTGTTGTTCTTGAAAACTAA | 3950 |
| AGATACATACCTGGTTTGCTTGGCT | 3975 |
| TACGTAAGAAAGTAGAAGAAAGTAA | 4000 |
| ACTGTAATAAATAAAAAAAAAAAA | 4025 |
| AAAAAA | 4031 |

FIG. 2(A)

```
         exon I
A1 CCATTCTGAGGGACGGGCGTA GAGTTCGGCCGAAGGAACCT GACCCAGGCTCTGTGAGGAG                                       27
                                                                   exon I  intron I
C1                                                                 GCAAG gtgag//..........GGATCGT CTCAGGTCAGCGGAGGGAGG   115
                                                                                          exon I A1 .........................................................//ctg gagctccaggaaccaggcag tgaggccttggt-------c tgagacagtatcctcaggtc
C1 AGACTTATAGACCTATCCAG TCTTCAAG gt//....//cag GTGCTCCAGAAAGCAGGAGT TGAAGACCTGGGTGTGAGGG ACACATACATCCTAAAAGCA   115
                        exon I   intron I    exon II A1 acagagcagaggatgcacag ggtgtgccagcagtgaatgt tt------gccctgaatgca caccaagggcccacctgcc acaggacacataggactcca
C1 CCACAGCAGGAGGAGGCCCAG GCAGTGCCAGGAGTCAAG gagtgcacgacctgactgtg taccaagggcctaccccca gaaacagtgtcagacctggc   70
                        exon II  intron II                                                                 158
                                                                                                       intron II exon II
A1 cagagtctggcctcacctcc ctactgtcagtcctgtagaa tcgac-ctctgctgccggc tgtacctga-gtaccctct cacttcctcctcttcag GTTTT
C1 agcaccggcccctgtagccac ccactgtcattctggtgcc tcatggctctgccagc tgtgcccgagggtgctttct cgcgtccttctacag GTTCC   70
                                                                                            intron III exon III   258

A1 CAGGGGACAGGCCAACCCAG AGGACAGGATTCCCTGGAGG CCACAGAGGAGCACC----A AGGAGAAGATCT gtaagtag gcctttgttagagtctccaa     1
C1 CAGAAGACAAACCCCCTAGG AAGACAGGCGACCTGTGAGG CCCTAGACACCACCCTTAAG AGAAGAAGAGCGTAAGCCG GCCTTTGTCAGAGCCATCAT   188
                                                                       exon III intron III                       M intron III exon III
A1 ggttcag-ttctcagctgag gccctctcacacactccctct ctccc-cag GCCTGTGGGTC TTCATTG-CCCAGCTCCTG CCACACTCCTGCCTGCTGCC
C1 GG gtgagtttctcagctgag gccactgccactgtccctct ctccctcagtcctgtgggat cccatcatacctattcgtgt tcacacgtttacctgctgct
exon III G intron III M    S    L    E    Q    R    S    L    H    C    K    P    E    E    A    L    E    A    Q    Q    E    A    L    G    L    V    C    V    28
A1           TCTCTTGAGCAGAGGAGTCT GCACTGCAAGCCTGAGGAAG CCCTTGAGGCCCAACAAGAG GCACTGGGGCCTGGTGTGTGT  286
C1 CT--GACGAGAGTCATCATG TCTCTTGAGCAGAGGAGTCT                                                                                                                            286
   cctgaacatattcatcatg                                 ccgcccagctgtttgagcaag gcttccagaaggcaatttc atactggagttggtagatgc Q    A    A    T    S    S    S    S    P    L    V    L    G    T    L    E    E    V    P    T    A    G    S    T    D    P    P    Q    S    P    Q    G    G    A    61
A1           GCAGGCTGCCACCTCCTCT CCTCTCCCTCTGGTCCTGGGC ACCCTGGAGGAGGTGCCCAC TGCTGGGGTCAACAGATCCTC CCCAGAGTCCTCAGGGAGCC   386
C1                                                                                                                                                                   386
   agaggatccccca S    A    F    P    T    T    I    N    F    T    R    Q    R    Q    P                                                                                         76
A1 TCCGGCCTTTCCCACTACCAT CAACTTCACTCGACAGAGGC AACCC-                                                                                                                   431
C1                                                 gatgaggaagaggag gaagcttcctccatttctc ttcctctttccactttttat
```

```
A1  ------------------------------------------------------------------------------------
C1  TCTCCAGAGATTCCTCAGAGTC  CTCCCTGAAGGGGAGAATACC  CATTCTCCTCTCCAGATTGT  TCCAAGTCTTCCTGAGTGGG  AGGACTCCCTGTCTCCTCAC    1894
    L  Q  I  P   Q  S  P  P  E  G  E  N  T   H  S  P  L  Q  I  V   P  S  L  P  E  W  E   D  S  L  S  P  H          546

A1  ------------------------------------------------------------------------------------
C1  TACTTTCCTCAGAGCCCTCC  TCAGGGGGAGGACTCCCTAT  CTCCTCACTACTTTCCTCAG  AGCCCTCCTCAGGGGAGGA  CTCCCTGTCTCCTCACTACT    1994
    Y  F  P   Q  S  P  P  Q  G  E  D  S  L  S   P  H  Y  F  P   Q  S  P  P  G  E  D   S  L  S  P  H  Y  F          580

A1  ------------------------------------------------------------------------------------
C1  TTCCTCAGAGCCCTCAGGGG  GAGGACTCCCTGTCTCCTCA  CTACTTTCCTCAGAGCCCTC  CTCAGGGGAGGACTCCATG  TCTCCTCTCTACTTTCCTCA    2094
    P   Q  S  P  Q  G  E  D  S  L  S  P  H   Y  F  P   Q  S  P  P  Q  G  E  D  S  M   S  P  L  Y  F  P   Q        613

A1  ------------------------------------------------------------------------------------
C1  GAGTCCCTCCTCAGGGGAGG  AATTCCAGTCTCTTCTCCAG  AGCCCTGTGAGCATCCAGTC  CTCTCCACTCCACTCCAGTC  CTCCCCAGAGTTTCCTGAG    2194
    S  P  L  Q  G  E  E   F  Q  S  S  L   Q  S  P   V  S  I  C  S   S  S  T  P  S  S  L   P  Q  S  F  P  E        646

A1  ------------------------------------------------------------------------------------
C1  AGTTCTCAGAGTCCTCCTGA  GGGGCCTGTCCAGTCTCCTC  TCCATAGTCCTCAGAGCCCT  CCTGAGGGGATGCACTCCCA  ATCTCCTCTCCAGAGTCCTG    2294
    S  S  Q   S  P  P  E   G  P  V  Q  S  P  L   H  S  P   Q  S  P  P  E  G  M  H  S  Q   S  P  L  Q  S  P  E    680

A1  ------------------------------------------------------------------------------------
C1  AGAGTGCTCCTGAGGGGGAG  GATTCCCTGTCCTCCTCTCCA  AATTCCCTCAGAGTCCTCTTG  AGGGAGAGGACTCCCTGTCT  TCTCCATTTCCTCAGAG    2394
    S  A  P  E  G  E   D  S  L  S  P  L  Q   I  P   Q  S  P  L  E   G  E  D  S  L  S   S  L  H  F  P   Q  S       713

A1  ------------------------------------------------------------------------------------
C1  TCCTCCTGAGTGTGGGAGGACT  CCCTCTCTCCACTTT  CCTCAGTTTCCTCCTCCAGGG  GGAGGACTTCCAGTCTTCTC  TCCAGAGTCCTGTGAGTATC    2494
    P  P  E  W  E  D  S   L  S  P  L  H  F   P   Q  F  P  P  Q  G   E  D  F  Q  S  S  L   Q  S  P   V  S  I       746

A1  ------------------------------------------------------------------------------------
C1  TGCTCCTCCTCCACTTCTTT  GAGTCTTCCCCAGAGTTTCC  CTGAGAGTCCTCAGAGTCCT  CCTGAGGGGCTGCTCAGTC  TCCTCCAGAGACCTGTCA    2594
    C  S  S  S  T  S  L   S  L  P  Q  S  F  P   E  S  P  Q   S  P   E  G  P  A  Q  S   P  L  Q  R  P   V  S       780

A1  ------------------------------------------------------------------------------------
C1  GCTCCTCTTCTCCTACACT  TTAGCGAGTCTTCTCCAAAG  TTCCCATGAGAGTCTTCCAGA  GTCCTCCTGAGGGCCTGCC  CAGTGCTCCTCCAGAGTCC    2694
    S  F  F  S  Y  T   L  A  S  L  L  S   H  E  S  P  Q   S  P  P  E  G  P  A   Q  S  P  L  Q  S  P         813
```

```
    Q  D  L  V  Q  E  K     Y  L  E  Y  R  Q  V     P  D  S  D  P  A     R  Y  E  F  L  W  G     P  R  A  L  A  E  T  274
A1 CAAGATTTGGTGCAGGAAAA GTACCTGGAGTACCGGCAGG TGCCGGACAGTGATCCCGCA CGCTATGAGTTCCTGTGGGG TCCAAGGGCCCTCGCTGAAA 1023
C1 AAAGTTTGGGTGCAGGAACA TTACCTAGAGTACCGGGAGG TGCCCAACTCTTCTCCTCCT CGTTACGAATTCCTGTGGGG TCCAAGAGCTCATTCAGAAG 3491
    K  V  W  V  Q  E  H     Y  L  E  Y  R  E  V     P  N  S  S  P  P     R  Y  E  F  L  W  G     P  R  A  H  S  E  V  1079

S  Y  Y  K  V  L        E  Y  V  I  K  V  S        A  R  V  R  F  F  F     P  S  L  R  E  A     A  L  R  E  E  E  E     307
A1 CCAGCTATGTGAAAGTCCTT GAGTATGTGATCAAGGTCAG TGCAAGAGTTCGCTTTTTCT TCCCATCCCTGCGTGAAGCA GCTTTGAGAGAGGAGGAAGA 1123
C1 TCATTAAGAGGAAAGTAGTA GAGTTTTTGGCCATGCTAAA GAATACCGTCCCTATTACCT TTCCATCTCTTACAAGGAT GCTTTGAAAGATGTGGAAGA 3591
    I  K  R  K  V  V        E  F  L  A  M  L  K        N  T  V  P  I  T  F     P  S  S  Y  K  D     A  L  K  D  V  E  E  E  1112

G  V  OPA                                                                                                                   309
A1 GGGAGTCTGAGCATGAGTTG CAGCCAAGGCCAGTGGGAGG GGGACTGGGCCAGTGCACCT TCCAGGGCCGCGTCCAGCAG CTTCCCCTGCCTCTGTGTGAC 1223
C1 GAGAGCCCAGGGCCATAATTG ACACCACAGATGATTCGACT GCCACAGAAAGTGCAAGCTC CAGTGTCATGTCCCCCAGCT TCTCTTCTGAGTGAAGTCTA 3691
    R  A  Q  A  I  I  D     T  T  D  D  S  T        A  T  E  S  A  S  S       S  V  M  S  P  S  F     S  S  E  OPA          1142

A1 ---ATGAGGCCCATTCTTCA CTCTGAAGAGAGCGGTCAGT GTTCTCAGTAGTAG------ -------------------- --------------GTTTC 1279
C1 GGGCAGATTCTTCCCTCTGA GTTTGAAGGGGGCAGTCGAG TTTCTACGTGGTGGAGAGAAC ACAGTGCTATTGCATTTCT 3791

A1 TGTTCTATTGGGTGACTTGG AGATTTATCTTTGTTCTCTT TTGGAATTGTTCAAATGTTT TT--TTTTAAGGGATGGTTG AATGAACTTCAGCATCCAAG 1377
C1 GTTCCATATGGGTAGTTATG GGGTTTACCTGTTTTACTTT TGGGTATTTTTCAAATGCTT TTCCTATTATTAATAACAGGTTT AAATAGCTTCAGAATCCTAG 3891

A1 TTTATGAATGACACAGCAGT-C ACACAGTTCTGTGTATATAG TTTAAGGGTAAGAGAGTCTGT GTTTTATTCAGATTGGGAAA TCCATTCTATTTTGTGAATT 1476
C1 TTTATGCACATGAGTCGCAC ATGTATTGCTGTGTTTTCGG TTTAAGAGTAACAGTTTGAT ATTTTGTAAAAACAAAAACA CACCCAAAACACACCACATTG 3991

A1 GGGATAATAACACAGCAGTGA ATAAGTACTTAGAAGTGTGA AAAATGAGCAGTAAAATAGA TGAGATAAAGAACTAAAGAA ATTAAGAGATAGTCAATTCT 1576
C1 GGAAAACCTTCTGCCTCATT TTGTGATGTGTCACAGGTTA ATGTGGTGTTACTGTAGGAA TTTTCTTGAAACTGTGAAGG AACTCTGCAGTTAAATAGTG 4091

A1 TGCCTTATACCTCAGTCTAT TCTGTAAAATTTTTAAAGAT ATATGCATACCTGGATTCC TTGGCTTCTTTGAGAATGTA AGAGAAATTAAATCTGAATA 1676
C1 GAATAAAGTAAAGGATTGTT AATGTTTGCATTTCCTCAGG TCCTTTAGTCTGTGTTCTT GAAAACTAAAGATACATACC TGGTTTGCTTGGCTTACGTA 4191

A1 AAGAATTCTTCCTGT-----                                                                                                     1691
C1 AGAAAGTAGAAGAAAGTAAA CTGTAATAAATAAA                                                                                       4225
```

5,997,872

SEQUENCE LISTING (1) GENERAL INFORMATION:

(iii) NUMBER OF SEQUENCES: 14

(2) INFORMATION FOR SEQ ID NO: 1:

(i) SEQUENCE CHARACTERISTICS:
      (A) LENGTH: 4031 base pairs
      (B) TYPE: nucleic acid
      (C) STRANDEDNESS: double-stranded
      (D) TOPOLOGY: linear (xi) SEQUENCE DESCRIPTION: SEQ ID NO: 1:

```
GGATCGTCTC AGGTCAGCGG AGGGAGGAGA CTTATAGACC TATCCAGTCT TCAAGGTGCT      60

CCAGAAAGCA GGAGTTGAAG ACCTGGGTGT GAGGGACACA TACATCCTAA AAGCACCACA     120

GCAGAGGAGG CCCAGGCAGT GCCAGGAGTC AAGGTTCCCA GAAGACAAAC CCCCTAGGAA     180

GACAGGCGAC CTGTGAGGCC CTAGAGCACC ACCTTAAGAG AAGAAGAGCT GTAAGCCGGC     240

CTTTGTCAGA GCCATCATGG GGGACAAGGA TATGCCTACT GCTGGGATGC CGAGTCTTCT     300

CCAGAGTTCC TCTGAGAGTC CTCAGAGTTG TCCTGAGGGG GAGGACTCCC AGTCTCCTCT     360

CCAGATTCCC CAGAGTTCTC CTGAGAGCGA CGACACCCTG TATCCTCTCC AGAGTCCTCA     420

GAGTCGTTCT GAGGGGAGG ACTCCTCGGA TCCTCTCCAG AGACCTCCTG AGGGGAAGGA      480

CTCCCAGTCT CCTCTCCAGA TTCCCCAGAG TTCCTCCTGAG GGCGACGACA CCCAGTCTCC    540

TCTCCAGAAT TCTCAGAGTT CTCCTGAGGG GAAGGACTCC CTGTCTCCTC TAGAGATTTC     600

TCAGAGCCCT CCTGAGGGTG AGGATGTCCA GTCTCCTCTG CAGAATCCTG CGAGTTCCTT     660

CTTCTCCTCT GCTTTATTGA GTATTTTCCA GAGTTCCCCT GAGAGAACTC AGAGTACTTT     720

TGAGGGTTTT CCCCAGTCTC CTCTCCAGAT TCCTGTGAGC TCCTCCTCCT CCTCCACTTT     780

ATTGAGTCTT TTCCAGAGTT CCCCTGAGAG AACTCAGAGT ACTTTTGAGG GTTTTCCCCA     840

GTCTCTTCTC CAGATTCCTA TGACCTCCTC CTTCTCCTCT ACTTTATTGA GTATTTTCCA     900

GAGTTCTCCT GAGAGTGCTC AAAGTACTTT TGAGGGTTTT CCCCAGTCTC CTCTCCAGAT     960

TCCTGGGAGC CCCTCCTTCT CCTCCACTTT ACTGAGTCTT TTCCAGAGTT CCCCTGAGAG    1020

AACTCACAGT ACTTTTGAGG GTTTTCCCCA GTCTCCTCTC CAGATTCCTA TGACCTCCTC    1080

CTTCTCCTCT ACTTTATTGA GTATTTTCCA GAGTTCTCCT GAGAGTGCTC AAAGTACTTT    1140

TGAGGGTTTT CCCCAGTCTC CTCTCCAGAT TCCTGGGAGC CCCTCCTTCT CCTCCACTTT    1200

ACTGAGTCTT TTCCAGAGTT CCCCTGAGAG AACTCACAGT ACTTTTGAGG GTTTTCCCCA    1260

GTCTCCTCTC CAGATTCCTA TGACCTCCTC CTTCTCCTCT ACTTTATTGA GTATTTTACA    1320

GAGTTCTCCT GAGAGTGCTC AAAGTGCTTT TGAGGGTTTT CCCCAGTCTC CTCTCCAGAT    1380

TCCTGTGAGC TCCTCTTTCT CCTACACTTT ATTGAGTCTT TTCCAGAGTT CCCCTGAGAG    1440

AACTCAGAGT ACTTTTGAGG GTTTTCCCCA GTCTCCTCTC CAGATTCCTG TGAGCTCCTC    1500

CTCCTCCTCC TCCACTTTAT TGAGTCTTTT CCAGAGTTCC CCTGAGTGTA CTCAAAGTAC    1560

TTTTGAGGGT TTTCCCCAGT CTCCTCTCCA GATTCCTCAG AGTCCTCCTG AAGGGGAGAA    1620

TACCCATTCT CCTCTCCAGA TTGTTCCAAG TCTTCCTGAG TGGGAGGACT CCCTGTCTCC    1680

TCACTACTTT CCTCAGAGCC CTCCTCAGGG GGAGGACTCC CTATCTCCTC ACTACTTTCC    1740

TCAGAGCCCT CCTCAGGGGG AGGACTCCCT GTCTCCTCAC TACTTTCCTC AGAGCCCTCA    1800

GGGGGAGGAC TCCCTGTCTC CTCACTACTT TCCTCAGAGC CCTCCTCAGG GGGAGGACTC    1860
```

```
CATGTCTCCT CTCTACTTTC CTCAGAGTCC TCTTCAGGGG GAGGAATTCC AGTCTTCTCT    1920

CCAGAGCCCT GTGAGCATCT GCTCCTCCTC CACTCCATCC AGTCTTCCCC AGAGTTTCCC    1980

TGAGAGTTCT CAGAGTCCTC CTGAGGGGCC TGTCCAGTCT CCTCTCCATA GTCCTCAGAG    2040

CCCTCCTGAG GGGATGCACT CCCAATCTCC TCTCCAGAGT CCTGAGAGTG CTCCTGAGGG    2100

GGAGGATTCC CTGTCTCCTC TCCAAATTCC TCAGAGTCCT CTTGAGGGAG AGGACTCCCT    2160

GTCTTCTCTC CATTTTCCTC AGAGTCCTCC TGAGTGGGAG GACTCCCTCT CTCCTCTCCA    2220

CTTTCCTCAG TTTCCTCCTC AGGGGAGGA CTTCCAGTCT TCTCTCCAGA GTCCTGTGAG    2280

TATCTGCTCC TCCTCCACTT CTTTGAGTCT TCCCCAGAGT TTCCCTGAGA GTCCTCAGAG    2340

TCCTCCTGAG GGGCCTGCTC AGTCTCCTCT CCAGAGACCT GTCAGCTCCT TCTTCTCCTA    2400

CACTTTAGCG AGTCTTCTCC AAAGTTCCCA TGAGAGTCCT CAGAGTCCTC CTGAGGGGCC    2460

TGCCCAGTCT CCTCTCCAGA GTCCTGTGAG CTCCTTCCCC TCCTCCACTT CATCGAGTCT    2520

TTCCCAGAGT TCTCCTGTGA GCTCCTTCCC CTCCTCCACT TCATCGAGTC TTTCCAAGAG    2580

TTCCCCTGAG AGTCCTCTCC AGAGTCCTGT GATCTCCTTC TCCTCCTCCA CTTCATTGAG    2640

CCCATTCAGT GAAGAGTCCA GCAGCCCAGT AGATGAATAT ACAAGTTCCT CAGACACCTT    2700

GCTAGAGAGT GATTCCTTGA CAGACAGCGA GTCCTTGATA GAGAGCGAGC CCTTGTTCAC    2760

TTATACACTG GATGAAAAGG TGGACGAGTT GGCGCGGTTT CTTCTCCTCA AATATCAAGT    2820

GAAGCAGCCT ATCACAAAGG CAGAGATGCT GACGAATGTC ATCAGCAGGT ACACGGGCTA    2880

CTTTCCTGTG ATCTTCAGGA AAGCCCGTGA GTTCATAGAG ATACTTTTTG GCATTTCCCT    2940

GAGAGAAGTG GACCCTGATG ACTCCTATGT CTTTGTAAAC ACATTAGACC TCACCTCTGA    3000

GGGGTGTCTG AGTGATGAGC AGGGCATGTC CCAGAACCGC CTCCTGATTC TTATTCTGAG    3060

TATCATCTTC ATAAAGGGCA CCTATGCCTC TGAGGAGGTC ATCTGGGATG TGCTGAGTGG    3120

AATAGGGGTG CGTGCTGGGA GGGAGCACTT TGCCTTTGGG GAGCCCAGGG AGCTCCTCAC    3180

TAAAGTTTGG GTGCAGGAAC ATTACCTAGA GTACCGGGAG GTGCCCAACT CTTCTCCTCC    3240

TCGTTACGAA TTCCTGTGGG GTCCAAGAGC TCATTCAGAA GTCATTAAGA GGAAAGTAGT    3300

AGAGTTTTTG GCCATGCTAA AGAATACCGT CCCTATTACC TTTCCATCCT CTTACAAGGA    3360

TGCTTTGAAA GATGTGGAAG AGAGAGCCCA GGCCATAATT GACACCACAG ATGATTCGAC    3420

TGCCACAGAA AGTGCAAGCT CCAGTGTCAT GTCCCCCAGC TTCTCTTCTG AGTGAAGTCT    3480

AGGGCAGATT CTTCCCTCTG AGTTTGAAGG GGGCAGTCGA GTTTCTACGT GGTGGAGGGC    3540

CTGGTTGAGG CTGGAGAGAA CACAGTGCTA TTTGCATTTC TGTTCCATAT GGGTAGTTAT    3600

GGGGTTTACC TGTTTTACTT TTGGGTATTT TTCAAATGCT TTTCCTATTA ATAACAGGTT    3660

TAAATAGCTT CAGAATCCTA GTTTATGCAC ATGAGTCGCA CATGTATTGC TGTTTTTCTG    3720

GTTTAAGAGT AACAGTTTGA TATTTTGTAA AAACAAAAAC ACACCCAAAC ACACCACATT    3780

GGGAAAACCT TCTGCCTCAT TTTGTGATGT GTCACAGGTT AATGTGGTGT TACTGTAGGA    3840

ATTTTCTTGA AACTGTGAAG GAACTCTGCA GTTAAATAGT GGAATAAAGT AAAGGATTGT    3900

TAATGTTTGC ATTTCCTCAG GTCCTTTAGT CTGTTGTTCT TGAAAACTAA AGATACATAC    3960

CTGGTTTGCT TGGCTTACGT AAGAAAGTAG AAGAAAGTAA ACTGTAATAA ATAAAAAAAA    4020

AAAAAAAAA A                                                         4031
```

(2) INFORMATION FOR SEQ ID NO: 2:

(i) SEQUENCE CHARACTERISTICS:
       (A) LENGTH: 12 base pairs
       (B) TYPE: nucleic acid (C) STRANDEDNESS: single-stranded
        (D) TOPOLOGY: linear (xi) SEQUENCE DESCRIPTION: SEQ ID NO: 2:

GATCTGCGGT GA                                                          12

(2) INFORMATION FOR SEQ ID NO: 3:

(i) SEQUENCE CHARACTERISTICS:
        (A) LENGTH: 12 base pairs
        (B) TYPE: nucleic acid
        (C) STRANDEDNESS: SINGLE-stranded
        (D) TOPOLOGY: linear (xi) SEQUENCE DESCRIPTION: SEQ ID NO: 3:

GATCTGTTCA TG                                                          12

(2) INFORMATION FOR SEQ ID NO: 4:

(i) SEQUENCE CHARACTERISTICS:
        (A) LENGTH: 12 base pairs
        (B) TYPE: nucleic acid
        (C) STRANDEDNESS: single-stranded
        (D) TOPOLOGY: linear (xi) SEQUENCE DESCRIPTION: SEQ ID NO: 4:

GATCTTCCCT CG                                                          12

(2) INFORMATION FOR SEQ ID NO: 5:

(i) SEQUENCE CHARACTERISTICS:
        (A) LENGTH: 46 base pairs
        (B) TYPE: nucleic acid
        (C) STRANDEDNESS: single-stranded
        (D) TOPOLOGY: linear (xi) SEQUENCE DESCRIPTION: SEQ ID NO: 5:

NAACTGGAAG AATTCGCGGC CGCAGGAATT TTTTTTTTTT TTTTTT                     46

(2) INFORMATION FOR SEQ ID NO: 6:

(i) SEQUENCE CHARACTERISTICS:
        (A) LENGTH: 12 base pairs
        (B) TYPE: nucleic acid
        (C) STRANDEDNESS: single-stranded
        (D) TOPOLOGY: linear (ix) FEATURE:
        (D) OTHER INFORMATION: BstX1 adapter upper strand (xi) SEQUENCE DESCRIPTION: SEQ ID NO: 6:

CTTTCCAGCA CA                                                          12

(2) INFORMATION FOR SEQ ID NO: 7:

(i) SEQUENCE CHARACTERISTICS:
        (A) LENGTH: 1142
        (B) TYPE: amino acids
        (C) STRANDEDNESS: single-stranded
        (D) TOPOLOGY: linear (xi) SEQUENCE DESCRIPTION: SEQ ID NO: 7:

Met Gly Asp Lys Asp Met Pro Thr Ala Gly Met Pro Ser Leu Leu Gln
                 5                  10                  15

Ser Ser Ser Glu Ser Pro Gln Ser Cys Pro Glu Gly Glu Asp Ser Gln
             20                  25                  30

Ser Pro Leu Gln Ile Pro Gln Ser Ser Pro Glu Ser Asp Asp Thr Leu

```
                35                  40                  45
Tyr Pro Leu Gln Ser Pro Gln Ser Arg Ser Glu Gly Glu Asp Ser Ser
                50                  55                  60
Asp Pro Leu Gln Arg Pro Pro Glu Gly Lys Asp Ser Gln Ser Pro Leu
 65                  70                  75                  80
Gln Ile Pro Gln Ser Ser Pro Glu Gly Asp Asp Thr Gln Ser Pro Leu
                    85                  90                  95
Gln Asn Ser Gln Ser Ser Pro Glu Gly Lys Asp Ser Leu Ser Pro Leu
                100                 105                 110
Glu Ile Ser Gln Ser Pro Pro Gly Glu Asp Val Gln Ser Pro Leu
                115                 120                 125
Gln Asn Pro Ala Ser Ser Phe Phe Ser Ser Ala Leu Leu Ser Ile Phe
130                 135                 140
Gln Ser Ser Pro Glu Ser Ile Gln Ser Pro Phe Glu Gly Phe Pro Gln
145                 150                 155                 160
Ser Val Leu Gln Ile Pro Val Ser Ala Ala Ser Ser Ser Thr Leu Val
                    165                 170                 175
Ser Ile Phe Gln Ser Ser Pro Gly Ser Thr Gln Ser Pro Phe Glu Gly
                    180                 185                 190
Phe Pro Gln Ser Pro Leu Gln Ile Pro Val Ser Arg Ser Phe Ser Ser
                195                 200                 205
Thr Leu Leu Ser Ile Phe Gln Ser Pro Glu Arg Ser Gln Arg Thr
210                 215                 220
Ser Glu Gly Phe Ala Gln Ser Pro Leu Gln Ile Pro Val Ser Ser Ser
225                 230                 235                 240
Ser Ser Ser Thr Leu Leu Ser Leu Phe Gln Ser Ser Pro Glu Arg Thr
                    245                 250                 255
Gln Ser Thr Phe Glu Gly Phe Pro Gln Ser Pro Leu Gln Ile Pro Val
                    260                 265                 270
Ser Arg Ser Phe Ser Ser Thr Leu Leu Ser Ile Phe Gln Ser Ser Pro
            275                 280                 285
Glu Arg Thr Gln Ser Thr Phe Glu Gly Phe Ala Gln Ser Pro Leu Gln
            290                 295                 300
Ile Pro Val Ser Ser Ser Ser Ser Thr Leu Leu Ser Leu Phe Gln
305                 310                 315                 320
Ser Ser Pro Glu Arg Thr Gln Ser Thr Phe Glu Gly Phe Pro Gln Ser
                325                 330                 335
Leu Leu Gln Ile Pro Met Thr Ser Ser Phe Ser Ser Thr Leu Leu Ser
                340                 345                 350
Ile Phe Gln Ser Ser Pro Glu Ser Ala Gln Ser Thr Phe Glu Gly Phe
                355                 360                 365
Pro Gln Ser Pro Leu Gln Ile Pro Gly Ser Pro Ser Phe Ser Ser Thr
            370                 375                 380
Leu Leu Ser Leu Phe Gln Ser Ser Pro Glu Arg Thr His Ser Thr Phe
385                 390                 395                 400
Glu Gly Phe Pro Gln Ser Pro Leu Gln Ile Pro Met Thr Ser Ser Phe
                405                 410                 415
Ser Ser Thr Leu Leu Ser Ile Leu Gln Ser Ser Pro Glu Ser Ala Gln
                420                 425                 430
Ser Ala Phe Glu Gly Phe Pro Gln Ser Pro Leu Gln Ile Pro Val Ser
            435                 440                 445
Ser Ser Phe Ser Tyr Thr Leu Leu Ser Leu Phe Gln Ser Ser Pro Glu
            450                 455                 460
```

```
Arg Thr Gln Ser Thr Phe Glu Gly Phe Pro Gln Ser Pro Leu Gln Ile
465                 470                 475                 480

Pro Val Ser Ser Ser Ser Ser Ser Thr Leu Leu Ser Leu Phe Gln
            485                 490                 495

Ser Ser Pro Glu Cys Thr Gln Ser Thr Phe Glu Gly Phe Pro Gln Ser
            500                 505                 510

Pro Leu Gln Ile Pro Gln Ser Pro Glu Gly Glu Asn Thr His Ser
            515                 520                 525

Pro Leu Gln Ile Val Pro Ser Leu Pro Glu Trp Glu Asp Ser Leu Ser
530                 535                 540

Pro His Tyr Phe Pro Gln Ser Pro Gln Gly Glu Asp Ser Leu Ser
545                 550                 555                 560

Pro His Tyr Phe Pro Gln Ser Pro Gln Gly Glu Asp Ser Leu Ser
            565                 570                 575

Pro His Tyr Phe Pro Gln Ser Pro Gln Gly Glu Asp Ser Leu Ser Pro
            580                 585                 590

His Tyr Phe Pro Gln Ser Pro Pro Gln Gly Glu Asp Ser Met Ser Pro
            595                 600                 605

Leu Tyr Phe Pro Gln Ser Pro Leu Gln Gly Glu Glu Phe Gln Ser Ser
            610                 615                 620

Leu Gln Ser Pro Val Ser Ile Cys Ser Ser Ser Thr Pro Ser Ser Leu
625                 630                 635                 640

Pro Gln Ser Phe Pro Glu Ser Ser Gln Ser Pro Pro Glu Gly Pro Val
                645                 650                 655

Gln Ser Pro Leu His Ser Pro Gln Ser Pro Pro Glu Gly Met His Ser
            660                 665                 670

Gln Ser Pro Leu Gln Ser Pro Glu Ser Ala Pro Glu Gly Glu Asp Ser
            675                 680                 685

Leu Ser Pro Leu Gln Ile Pro Gln Ser Pro Leu Glu Gly Glu Asp Ser
            690                 695                 700

Leu Ser Ser Leu His Phe Pro Gln Ser Pro Pro Glu Trp Glu Asp Ser
705                 710                 715                 720

Leu Ser Pro Leu His Phe Pro Gln Phe Pro Pro Gln Gly Glu Asp Phe
                725                 730                 735

Gln Ser Ser Leu Gln Ser Pro Val Ser Ile Cys Ser Ser Ser Thr Ser
                740                 745                 750

Leu Ser Leu Pro Gln Ser Phe Pro Glu Ser Pro Gln Ser Pro Pro Glu
            755                 760                 765

Gly Pro Ala Gln Ser Pro Leu Gln Arg Pro Val Ser Ser Phe Phe Ser
            770                 775                 780

Tyr Thr Leu Ala Ser Leu Leu Gln Ser Ser His Glu Ser Pro Gln Ser
785                 790                 795                 800

Pro Pro Glu Gly Pro Ala Gln Ser Pro Leu Gln Ser Pro Val Ser Ser
                805                 810                 815

Phe Pro Ser Ser Thr Ser Ser Ser Leu Ser Gln Ser Ser Pro Val Ser
            820                 825                 830

Ser Phe Pro Ser Ser Thr Ser Ser Ser Leu Ser Lys Ser Ser Pro Glu
            835                 840                 845

Ser Pro Leu Gln Ser Pro Val Ile Ser Phe Ser Ser Ser Thr Ser Leu
            850                 855                 860

Ser Pro Phe Ser Glu Glu Ser Ser Pro Val Asp Glu Tyr Thr Ser
865                 870                 875                 880

Ser Ser Asp Thr Leu Leu Glu Ser Asp Ser Leu Thr Asp Ser Glu Ser
                885                 890                 895
```

```
Leu Ile Glu Ser Glu Pro Leu Phe Thr Tyr Thr Leu Asp Glu Lys Val
            900                 905                 910

Asp Glu Leu Ala Arg Phe Leu Leu Leu Lys Tyr Gln Val Lys Gln Pro
            915                 920                 925

Ile Thr Lys Ala Glu Met Leu Thr Asn Val Ile Ser Arg Tyr Thr Gly
            930                 935                 940

Tyr Phe Pro Val Ile Phe Arg Lys Ala Arg Glu Phe Ile Glu Ile Leu
945                 950                 955                 960

Phe Gly Ile Ser Leu Arg Glu Val Asp Pro Asp Ser Tyr Val Phe
            965                 970                 975

Val Asn Thr Leu Asp Leu Thr Ser Glu Gly Cys Leu Ser Asp Glu Gln
            980                 985                 990

Gly Met Ser Gln Asn Arg Leu Leu Ile Leu Ile Leu Ser Ile Ile Phe
            995                 1000                1005

Ile Lys Gly Thr Tyr Ala Ser Glu Glu Val Ile Trp Asp Val Leu Ser
            1010                1015                1020

Gly Ile Gly Val Arg Ala Gly Arg Glu His Phe Ala Phe Gly Glu Pro
1025                1030                1035                1040

Arg Glu Leu Leu Thr Lys Val Trp Val Gln Glu His Tyr Leu Glu Tyr
            1045                1050                1055

Arg Glu Val Pro Asn Ser Ser Pro Pro Arg Tyr Glu Phe Leu Trp Gly
            1060                1065                1070

Pro Arg Ala His Ser Glu Val Ile Lys Arg Lys Val Val Glu Phe Leu
            1075                1080                1085

Ala Met Leu Lys Asn Thr Val Pro Ile Thr Phe Pro Ser Ser Tyr Lys
            1090                1095                1100

Asp Ala Leu Lys Asp Val Glu Glu Arg Ala Gln Ala Ile Ile Asp Thr
1105                1110                1115                1120

Thr Asp Asp Ser Thr Ala Thr Glu Ser Ala Ser Ser Ser Val Met Ser
            1125                1130                1135

Pro Ser Phe Ser Ser Glu
            1140

(2) INFORMATION FOR SEQ ID NO: 8:

(i) SEQUENCE CHARACTERISTICS:
        (A) LENGTH: 1691 base pairs
        (B) TYPE: nucleotides
        (C) STRANDEDNESS: single stranded
        (D) TOPOLOGY: linear (xi) SEQUENCE DESCRIPTION: SEQ ID NO: 8:

CCATTCTGAG GGACGGCGTA GAGTTCGGCC GAAGGAACCT GACCCAGGCT CTGTGAGGAG      60

GCAAGGTTTT CAGGGGACAG GCCAACCCAG AGGACAGGAT TCCCTGGAGG CCACAGAGGA    120

GCACCAAGGA GAAGATCTGC CTGTGGGTCT TCATTGCCCA GCTCCTGCCC ACACTCCTGC    180

CTGCTGCCCT GACGAGAGTC ATCATGTCTC TTGAGCAGAG GAGTCTGCAC TGCAAGCCTG    240

AGGAAGCCCT TGAGGCCCAA CAAGAGGCCC TGGGCCTGGT GTGTGTGCAG GCTGCCACCT    300

CCTCCTCCTC TCCTCTGGTC CTGGGCACCC TGGAGGAGGT GCCCACTGCT GGGTCAACAG    360

ATCCTCCCCA GAGTCCTCAG GGAGCCTCCG CCTTTCCCAC TACCATCAAC TTCACTCGAC    420

AGAGGCAACC CAGTGAGGGT TCCAGCAGCC GTGAAGAGGA GGGGCCAAGC ACCTCTTGTA    480

TCCTGGAGTC CTTGTTCCGA GCAGTAATCA CTAAGAAGGT GGCTGATTTG GTTGGTTTTC    540

TGCTCCTCAA ATATCGAGCC AGGGAGCCAG TCACAAAGGC AGAAATGCTG GAGAGTGTCA    600
```

-continued

```
TCAAAAATTA CAAGCACTGT TTTCCTGAGA TCTTCGGCAA AGCCTCTGAG TCCTTGCAGC    660

TGGTCTTTGG CATTGACGTG AAGGAAGCAG ACCCCACCGG CCACTCCTAT GTCCTTGTCA    720

CCTGCCTAGG TCTCTCCTAT GATGGCCTGC TGGGTGATAA TCAGATCATG CCCAAGACAG    780

GCTTCCTGAT AATTGTCCTG GTCATGATTG CAATGGAGGG CGGCCATGCT CCTGAGGAGG    840

AAATCTGGGA GGAGCTGAGT GTGATGGAGG TGTATGATGG GAGGGAGCAC AGTGCCTATG    900

GGGAGCCCAG GAAGCTGCTC ACCCAAGATT TGGTGCAGGA AAAGTACCTG GAGTACCGGC    960

AGGTGCCGGA CAGTGATCCC GCACGCTATG AGTTCCTGTG GGGTCCAAGG GCCCTCGCTG   1020

AAACCAGCTA TGTGAAAGTC CTTGAGTATG TGATCAAGGT CAGTGCAAGA GTTCGCTTTT   1080

TCTTCCCATC CCTGCGTGAA GCAGCTTTGA GAGAGGAGGA AGAGGGAGTC TGAGCATGAG   1140

TTGCAGCCAA GGCCAGTGGG AGGGGACTG  GGCCAGTGCA CCTTCCAGGG CCGCGTCCAG   1200

CAGCTTCCCC TGCCTCGTGT GACATGAGGC CCATTCTTCA CTCTGAAGAG AGCGGTCAGT   1260

GTTCTCAGTA GTAGGTTTCT GTTCTATTGG GTGACTTGGA GATTTATCTT TGTTCTCTTT   1320

TGGAATTGTT CAAATGTTTT TTTTTAAGGG ATGGTTGAAT GAACTTCAGC ATCCAAGTTT   1380

ATGAATGACA GCAGTCACAC AGTTCTGTGT ATATAGTTTA AGGGTAAGAG TCTTGTGTTT   1440

TATTCAGATT GGGAAATCCA TTCTATTTTG TGAATTGGGA TAATAACAGC AGTGGAATAA   1500

GTACTTAGAA ATGTGAAAAA TGAGCAGTAA AATAGATGAG ATAAAGAACT AAAGAAATTA   1560

AGAGATAGTC AATTCTTGCC TTATACCTCA GTCTATTCTG TAAAATTTTT AAAGATATAT   1620

GCATACCTGG ATTTCCTTGG CTTCTTTGAG AATGTAAGAG AAATTAAATC TGAATAAAGA   1680

ATTCTTCCTG T                                                        1691
```

(2) INFORMATION FOR SEQ ID NO: 9:

(i) SEQUENCE CHARACTERISTICS:
        (A) LENGTH: 4225 base pairs
        (B) TYPE: nucleic acids
        (C) STRANDEDNESS: double-stranded
        (D) TOPOLOGY: linear (xi) SEQUENCE DESCRIPTION: SEQ ID NO: 9:

```
GGATCGTCTC AGGTCAGCGG AGGGAGGAGA CTTATAGACC TATCCAGTCT TCAAGGTGCT     60

CCAGAAAGCA GGAGTTGAAG ACCTGGGTGT GAGGGACACA TACATCCTAA AAGCACCACA    120

GCAGAGGAGG CCCAGGCAGT GCCAGGAGTC AAGGTTCCCA GAAGACAAAC CCCCTAGGAA    180

GACAGGCGAC CTGTGAGGCC CTAGAGCACC ACCTTAAGAG AAGAAGAGCT GTAAGCCGGC    240

CTTTGTCAGA GCCATCATGG GGGACAAGGA TATGCCTACT GCTGGGATGC CGAGTCTTCT    300

CCAGAGTTCC TCTGAGAGTC CTCAGAGTTG TCCTGAGGGG GAGGACTCCC AGTCTCCTCT    360

CCAGATTCCC CAGAGTTCTC CTGAGAGCGA CGACACCCTG TATCCTCTCC AGAGTCCTCA    420

GAGTCGTTCT GAGGGGGAGG ACTCCTCGGA TCCTCTCCAG AGACCTCCTG AGGGGAAGGA    480

CTCCCAGTCT CCTCTCCAGA TTCCCCAGAG TTCTCCTGAG GGCGACGACA CCCAGTCTCC    540

TCTCCAGAAT TCTCAGAGTT CTCCTGAGGG GAAGGACTCC CTGTCTCCTC TAGAGATTTC    600

TCAGAGCCCT CCTGAGGGTG AGGATGTCCA GTCTCCTCTG CAGAATCCTG CGAGTTCCTT    660

CTTCTCCTCT GCTTTATTGA GTATTTTCCA GAGTTCCCCT GAGAGTATTC AAAGTCCTTT    720

TGAGGGTTTT CCCCAGTCTG TTCTCCAGAT TCCTGTGAGC GCCGCCTCCT CCTCCACTTT    780

AGTGAGTATT TTCAGAGTT  CCCCTGAGAG TACTCAAAGT CCTTTTGAGG GTTTTCCCCA    840

GTCTCCACTC CAGATTCCTG TGAGCCGCTC CTTCTCCTCC ACTTTATTGA GTATTTTCCA    900

GAGTTCCCCT GAGAGAAGTC AGAGAACTTC TGAGGGTTTT GCACAGTCTC CTCTCCAGAT    960
```

```
TCCTGTGAGC TCCTCCTCGT CCTCCACTTT ACTGAGTCTT TTCCAGAGTT CCCCTGAGAG    1020

AACTCAGAGT ACTTTTGAGG GTTTTCCCCA GTCTCCACTC CAGATTCCTG TGAGCCGCTC    1080

CTTCTCCTCC ACTTTATTGA GTATTTTCCA GAGTTCCCCT GAGAGAACTC AGAGTACTTT    1140

TGAGGGTTTT GCCCAGTCTC CTCTCCAGAT TCCTGTGAGC TCCTCCTCCT CCTCCACTTT    1200

ATTGAGTCTT TTCCAGAGTT CCCCTGAGAG AACTCAGAGT ACTTTTGAGG GTTTTCCCCA    1260

GTCTCTTCTC CAGATTCCTA TGACCTCCTC CTTCTCCTCT ACTTTATTGA GTATTTTCCA    1320

GAGTTCTCCT GAGAGTGCTC AAAGTACTTT TGAGGGTTTT CCCCAGTCTC CTCTCCAGAT    1380

TCCTGGGAGC CCCTCCTTCT CCTCCACTTT ACTGAGTCTT TTCCAGAGTT CCCCTGAGAG    1440

AACTCACAGT ACTTTTGAGG GTTTTCCCCA GTCTCCTCTC CAGATTCCTA TGACCTCCTC    1500

CTTCTCCTCT ACTTTATTGA GTATTTTACA GAGTTCTCCT GAGAGTGCTC AAAGTGCTTT    1560

TGAGGGTTTT CCCCAGTCTC CTCTCCAGAT TCCTGTGAGC TCCTCTTTCT CCTACACTTT    1620

ATTGAGTCTT TTCCAGAGTT CCCCTGAGAG AACTCAGAGT ACTTTTGAGG GTTTTCCCCA    1680

GTCTCCTCTC CAGATTCCTG TGAGCTCCTC CTCCTCCTCC TCCACTTTAT TGAGTCTTTT    1740

CCAGAGTTCC CCTGAGTGTA CTCAAAGTAC TTTTGAGGGT TTTCCCCAGT CTCCTCTCCA    1800

GATTCCTCAG AGTCCTCCTG AAGGGGAGAA TACCCATTCT CCTCTCCAGA TTGTTCCAAG    1860

TCTTCCTGAG TGGGAGGACT CCCTGTCTCC TCACTACTTT CCTCAGAGCC CTCCTCAGGG    1920

GGAGGACTCC CTATCTCCTC ACTACTTTCC TCAGAGCCCT CCTCAGGGGG AGGACTCCCT    1980

GTCTCCTCAC TACTTTCCTC AGAGCCCTCA GGGGAGGAC TCCCTGTCTC CTCACTACTT    2040

TCCTCAGAGC CCTCCTCAGG GGGAGGACTC CATGTCTCCT CTCTACTTTC CTCAGAGTCC    2100

TCTTCAGGGG GAGGAATTCC AGTCTTCTCT CCAGAGCCCT GTGAGCATCT GCTCCTCCTC    2160

CACTCCATCC AGTCTTCCCC AGAGTTTCCC TGAGAGTTCT CAGAGTCCTC CTGAGGGGCC    2220

TGTCCAGTCT CCTCTCCATA GTCCTCAGAG CCCTCCTGAG GGGATGCACT CCCAATCTCC    2280

TCTCCAGAGT CCTGAGAGTG CTCCTGAGGG GGAGGATTCC CTGTCTCCTC TCCAAATTCC    2340

TCAGAGTCCT CTTGAGGGAG AGGACTCCCT GTCTTCTCTC CATTTTCCTC AGAGTCCTCC    2400

TGAGTGGGAG GACTCCCTCT CTCCTCTCCA CTTTCCTCAG TTTCCTCCTC AGGGGGAGGA    2460

CTTCCAGTCT TCTCTCCAGA GTCCTGTGAG TATCTGCTCC TCCTCCACTT CTTTGAGTCT    2520

TCCCCAGAGT TTCCCTGAGA GTCCTCAGAG TCCTCCTGAG GGGCCTGCTC AGTCTCCTCT    2580

CCAGAGACCT GTCAGCTCCT TCTTCTCCTA CACTTTAGCG AGTCTTCTCC AAAGTTCCCA    2640

TGAGAGTCCT CAGAGTCCTC CTGAGGGGCC TGCCCAGTCT CCTCTCCAGA GTCCTGTGAG    2700

CTCCTTCCCC TCCTCCACTT CATCGAGTCT TTCCAGAGT TCTCCTGTGA GCTCCTTCCC    2760

CTCCTCCACT TCATCGAGTC TTTCCAAGAG TTCCCCTGAG AGTCCTCTCC AGAGTCCTGT    2820

GATCTCCTTC TCCTCCTCCA CTTCATTGAG CCCATTCAGT GAAGAGTCCA GCAGCCCAGT    2880

AGATGAATAT ACAAGTTCCT CAGACACCTT GCTAGAGAGT GATTCCTTGA CAGACAGCGA    2940

GTCCTTGATA GAGAGCGAGC CCTTGTTCAC TTATACACTG GATGAAAAGG TGGACGAGTT    3000

GGCGCGGTTT CTTCTCCTCA AATATCAAGT GAAGCAGCCT ATCACAAAGG CAGAGATGCT    3060

GACGAATGTC ATCAGCAGGT ACACGGGCTA CTTTCCTGTG ATCTTCAGGA AAGCCCGTGA    3120

GTTCATAGAG ATACTTTTTG GCATTTCCCT GAGAGAAGTG GACCCTGATG ACTCCTATGT    3180

CTTTGTAAAC ACATTAGACC TCACCTCTGA GGGGTGTCTG AGTGATGAGC AGGGCATGTC    3240

CCAGAACCGC CTCCTGATTC TTATTCTGAG TATCATCTTC ATAAAGGGCA CCTATGCCTC    3300

TGAGGAGGTC ATCTGGGATG TGCTGAGTGG AATAGGGGTG CGTGCTGGGA GGGAGCACTT    3360
```

```
TGCCTTTGGG GAGCCCAGGG AGCTCCTCAC TAAAGTTTGG GTGCAGGAAC ATTACCTAGA    3420

GTACCGGGAG GTGCCCAACT CTTCTCCTCC TCGTTACGAA TTCCTGTGGG GTCCAAGAGC    3480

TCATTCAGAA GTCATTAAGA GGAAAGTAGT AGAGTTTTTG GCCATGCTAA AGAATACCGT    3540

CCCTATTACC TTTCCATCCT CTTACAAGGA TGCTTTGAAA GATGTGGAAG AGAGAGCCCA    3600

GGCCATAATT GACACCACAG ATGATTCGAC TGCCACAGAA AGTGCAAGCT CCAGTGTCAT    3660

GTCCCCCAGC TTCTCTTCTG AGTGAAGTCT AGGGCAGATT CTTCCCTCTG AGTTTGAAGG    3720

GGGCAGTCGA GTTTCTACGT GGTGGAGGGC CTGGTTGAGG CTGGAGAGAA CACAGTGCTA    3780

TTTGCATTTC TGTTCCATAT GGGTAGTTAT GGGGTTTACC TGTTTTACTT TTGGGTATTT    3840

TTCAAATGCT TTTCCTATTA ATAACAGGTT TAAATAGCTT CAGAATCCTA GTTTATGCAC    3900

ATGAGTCGCA CATGTATTGC TGTTTTTCTG GTTAAGAGT AACAGTTTGA TATTTTGTAA    3960

AAACAAAAAC ACACCCAAAC ACACCACATT GGGAAAACCT TCTGCCTCAT TTTGTGATGT    4020

GTCACAGGTT AATGTGGTGT TACTGTAGGA ATTTTCTTGA AACTGTGAAG GAACTCTGCA    4080

GTTAAATAGT GGAATAAAGT AAAGGATTGT TAATGTTTGC ATTTCCTCAG GTCCTTTAGT    4140

CTGTTGTTCT TGAAAACTAA AGATACATAC CTGGTTTGCT TGGCTTACGT AAGAAAGTAG    4200

AAGAAAGTAA ACTGTAATAA ATAAA                                          4225
```

(2) INFORMATION FOR SEQ ID NO: 10:

(i) SEQUENCE CHARACTERISTICS:
        (A) LENGTH: 309
        (B) TYPE: amino acids
        (C) STRANDEDNESS: single stranded
        (D) TOPOLOGY: linear (xi) SEQUENCE DESCRIPTION: SEQ ID NO: 10:

```
Met Ser Leu Glu Gln Arg Ser Leu His Cys Lys Pro Glu Glu Ala Leu
            5                  10                  15

Glu Ala Gln Gln Glu Ala Leu Gly Leu Val Cys Val Gln Ala Ala Thr
         20                  25                  30

Ser Ser Ser Ser Pro Leu Val Leu Gly Thr Leu Glu Glu Val Pro Thr
     35                  40                  45

Ala Gly Ser Thr Asp Pro Pro Gln Ser Pro Gln Gly Ala Ser Ala Phe
 50                  55                  60

Pro Thr Thr Ile Asn Phe Thr Arg Gln Arg Gln Pro Ser Glu Gly Ser
65                  70                  75                  80

Ser Ser Arg Glu Glu Glu Gly Pro Ser Thr Ser Cys Ile Leu Glu Ser
             85                  90                  95

Leu Phe Arg Ala Val Ile Thr Lys Lys Val Ala Asp Leu Val Gly Phe
        100                 105                 110

Leu Leu Leu Lys Tyr Arg Ala Arg Glu Pro Val Thr Lys Ala Glu Met
    115                 120                 125

Leu Glu Ser Val Ile Lys Asn Tyr Lys His Cys Phe Pro Glu Ile Phe
130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
            180                 185                 190

Gly Phe Leu Ile Ile Val Leu Val Met Ile Ala Met Glu Gly Gly His
        195                 200                 205
```

```
Ala Pro Glu Glu Glu Ile Trp Glu Glu Leu Ser Val Met Glu Val Tyr
    210                 215                 220

Asp Gly Arg Glu His Ser Ala Tyr Gly Glu Pro Arg Lys Leu Leu Thr
225                 230                 235                 240

Gln Asp Leu Val Gln Glu Lys Tyr Leu Glu Tyr Arg Gln Val Pro Asp
                245                 250                 255

Ser Asp Pro Ala Arg Tyr Glu Phe Leu Trp Gly Pro Arg Ala Leu Ala
            260                 265                 270

Glu Thr Ser Tyr Val Lys Val Leu Glu Tyr Val Ile Lys Val Ser Ala
        275                 280                 285

Arg Val Arg Phe Phe Phe Pro Ser Leu Arg Glu Ala Ala Leu Arg Glu
    290                 295                 300

Glu Glu Glu Gly Val
305             309
```

(2) INFORMATION FOR SEQ ID NO: 11:

(i) SEQUENCE CHARACTERISTICS:
        (A) LENGTH: 24 base pairs
        (B) TYPE: nucleic acid
        (C) STRANDEDNESS: single-stranded
        (D) TOPOLOGY: linear (xi) SEQUENCE DESCRIPTION: SEQ ID NO: 11:

AGCACTCTCC AGCCTCTCAC CGCA                             24

(2) INFORMATION FOR SEQ ID NO: 12:

(i) SEQUENCE CHARACTERISTICS:
        (A) LENGTH: 24 base pairs
        (B) TYPE: nucleic acid
        (C) STRANDEDNESS: single-stranded
        (D) TOPOLOGY: linear (xi) SEQUENCE DESCRIPTION: SEQ ID NO: 12:

ACCGACGTCG ACTATCCATG AACA                             24

(2) INFORMATION FOR SEQ ID NO: 13:

(i) SEQUENCE CHARACTERISTICS:
        (A) LENGTH: 24 base pairs
        (B) TYPE: nucleic acid
        (C) STRANDEDNESS: single-stranded
        (D) TOPOLOGY: linear (xi) SEQUENCE DESCRIPTION: SEQ ID NO: 13:

AGGCAACTGT GCTATCCGAG GGAA                             24

(2) INFORMATION FOR SEQ ID NO: 14:

(i) SEQUENCE CHARACTERISTICS:
        (A) LENGTH: 8 base pairs
        (B) TYPE: nucleic acid
        (C) STRANDEDNESS: single-stranded
        (D) TOPOLOGY: linear (ix) FEATURE:
        (D) OTHER INFORMATION: BstX1 adapter lower strand (xi) SEQUENCE DESCRIPTION: SEQ ID NO: 14:

CTGGAAAG                                                     8

ISOLATED NUCLEIC ACID MOLECULE CODING FOR TUMOR REJECTION ANTIGEN PRECURSOR MAGE-C1 AND USES THEREOF

This is a divisional application of application Ser. No. 08/845,528 filed on Apr. 25, 1997.

FIELD OF THE INVENTION

This invention relates to a nucleic acid molecule which codes for a tumor rejection antigen precursor. More particularly, the invention concerns nucleic acid molecules which encode a tumor rejection antigen precursor which can be processed, inter alia, into peptides presented by many MHC molecules, such as HLA-A1 and its alleles, HLA-A2, HLA-Cw*1601, HLA-B44, and so forth. MAGE-C1, a preferred embodiment, shares partial homology with other members of the MAGE family known to date but is approximately 2 kb larger. MAGE-C1 TRAs are expressed on a variety of tumors and in normal testis cells, but are not expressed by other normal cells.

BACKGROUND AND PRIOR ART

The process by which the mammalian immune system recognizes and reacts to foreign or alien materials is a complex one. An important facet of the system is the T lymphocyte, or "T cell" response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunology* (J. P. Lipincott Company, 1987), especially chapters 6–10. The interaction of T cells and HLA/peptide complexes is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Much work has focused on the mechanisms by which proteins are processed into the HLA binding peptides. See in this regard, Barinaga, Science 257:880 (1992); Fremont et al., Science 257:919 (1992); Matsumura et al., Science 257:927 (1992); Latron et al., Science 257:964 (1992).

The mechanism by which T cells recognize cellular abnormalities has also been implicated in cancer. For example, in PCT application PCT/US92104354, filed May 22, 1992, published on Nov. 26, 1992, and incorporated by reference, a family of genes is disclosed, which are processed into peptides which, in turn, are expressed on cell surfaces, which can lead to lysis of the tumor cells by specific cytolytic T lymphocytes ("CTLs"). The genes are said to code for "tumor rejection antigen precursors" or "TRAP" molecules, and the peptides derived therefrom are referred to as "tumor rejection antigens" or "TRAs". See Traversari et al., Immunogenetics 35:145 (1992); van der Bruggen et al., Science 254:1643 (1991), for further information on this family of genes. Also, see U.S. Pat. Nos. 5,342,774 and 5,462,871 incorporated by reference in their entirety.

In U.S. Pat. No. 5,405,940 the disclosure of which is incorporated by reference, it is explained that the MAGE-1 gene codes for a tumor rejection antigen precursor, which is processed to nonapeptides which are presented by the HLA-A1 molecule. The nonapeptides which bind to HLA-A1 follow a "rule" for binding in that a motif is satisfied. In this regard, see e.g. PCT/US93/07421; Falk et al., Nature 351:290–296 (1991); Engelhard, Ann Rev. Immunol. 12:181–207 (1994); Ruppert et al., Cell 74:929–937 (1993); Rötzschke et al., Nature 348:252–254 (1990); Bjorkman et al., Nature 329:512–518 (1987); Traversari et al., J. Exp. Med. 176:1453–1457 (1992). The reference teaches that given the known specificity of particular peptides for particular HLA molecules, one should expect a particular peptide to bind to one HLA molecule, but not to others. Because different individuals possess different HLA phenotypes, identification of a particular peptide as being a partner for a particular HLA molecule has diagnostic and therapeutic ramifications, only for individuals with that particular HLA phenotype. There is a need for further work in the area, because cellular abnormalities are not restricted to one particular HLA phenotype, and targeted therapy requires some knowledge of the phenotype of the abnormal cells at issue.

In U.S. patent application Ser. No. 288,977, filed Aug. 11, 1994 now U.S. Pat. No. 5,629,166 and incorporated by reference, the fact that the MAGE-1 expression product is processed to a second TRA is disclosed. This second TRA is presented by HLA-Cw*1601 molecules. The disclosure shows that a given TRAP can yield a plurality of TRAs, each of which will satisfy a motif rule for binding to an MHC molecule.

In U.S. patent application Ser. No. 994,928, filed Dec. 22, 1992 now abandoned, and incorporated by reference herein teaches that tyrosinase, a molecule which is produced by some normal cells (e.g., melanocytes), is processed in tumor cells to yield peptides presented by HLA-A2 molecules.

In U.S. patent application Ser. No. 08/032,978, filed Mar. 18, 1993 now U.S. Pat. No. 5,620,886, and incorporated by reference in its entirety, a second TRA, not derived from tyrosinase is taught to be presented by HLA-A2 molecules. The TRA is derived from a TRAP, but is coded for by a non-MAGE gene. This disclosure shows that a particular HLA molecule may present TRAs derived from different sources.

In U.S. patent application Ser. No. 08/079,110, filed Jun. 17, 1993 now U.S. Pat. No. 5,571,711 issued Jan. 5, 1996 and incorporated by reference herein, an unrelated tumor rejection antigen precursor, the so-called "BAGE" precursor is described. The BAGE precursor is not related to the MAGE family.

In U.S. patent application Ser. Nos. 08/096,039 now abandoned and 08/250,162 now U.S. Pat. No. 5,610,013, both of which are incorporated by reference, a non-MAGE TRAP precursor, GAGE, is also disclosed.

U.S. application Ser. No. 08/316,231 filed Sep. 30, 1994 now U.S. Pat. No. 5,830,753, discloses that additional tumor rejection antigen precursors. These tumor rejection antigen precursors are referred to as "DAGE" tumor rejection antigen precursors. They do not show homology to the MAGE, the BAGE, or GAGE family of genes.

The work which is presented by the papers, patent, and patent applications cited supra deals, in large part, with the MAGE, BAGE, GAGE, and DAGE family of genes. The present invention relates to nucleic acid molecules encoding a MAGE-related tumor rejection antigen precursor, i.e., MAGE-C1, and to the tumor rejection antigen precursors and tumor rejection antigens themselves. The invention also relates to applications of both nucleic acid and protein molecules.

The invention is elaborated upon further in the disclosure which follows.

BRIEF DESCRIPTION OF THE FIGURES

FIG. 1 is the nucleotide sequence of MAGE-C1 cDNA. The position of various; nucleotide sense and antisense primers are indicated.

FIG. 2 depicts a comparison of the nucleotide sequences of MAGE-C1 and MAGE-A1.

DETAILED DESCRIPTION

Figure 3:
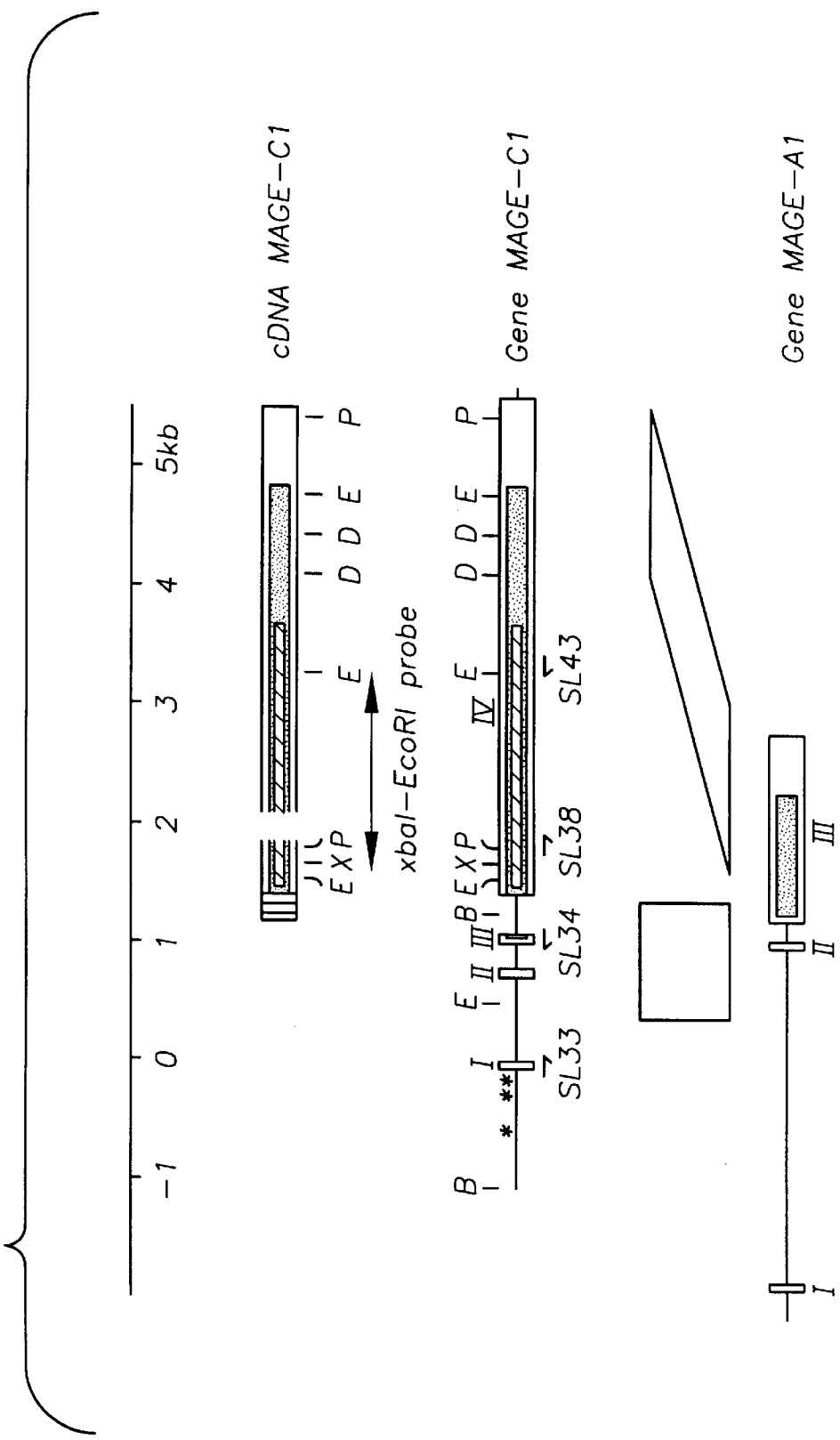
FIG. 3 is a comparison of gene MAGE-C1 with isolated cDNA clone MAGE-C1 and published gene MAGE-A1. Exons appear as boxes and are numbered from I to III (MAGE-A1) or IV (MAGE-C1). Introns appear as lines. Deletion in the cDNA clone as compared to gene MAGE-C1 appears as a blank. Similar regions between genes MAGE-A1 and MAGE-C1 are indicated by shaded areas. Open reading frames are indicated by dark boxes inside the exons. Repeated segments in gene MAGE-C1 are shown as a hatched box. Important restriction sites are indicated (B: BamHI, D: Dpnll, E: EcoRl, P: Pstl, X: XbaI), as well as positions of two pairs of oligonucleotides (SL33/SL34, and SL38/SL43). Asterix upstream from MAGE-C1 exon I show localization of the Spl and the 2 Ets consensus recognition sequences. The position of the XbaI-EcoRl cDNA probe is also indicated.

The examples of this invention show the isolation of a nucleic acid molecule which codes for a tumor rejection antigen precursor ("TRAP"), MAGE-C1. This TRAP encoding molecule shares partial homology with the MAGE family coding sequences described in the references set forth supra. Hence, one aspect of the invention is an isolated nucleic acid molecule which encodes a protein having the amino acid sequence encoded by the nucleotide sequence set forth in SEQ ID NO:9. Preferably the nucleic acid molecule is a cDNA molecule. SEQ ID NO:9 is not a previously known MAGE, BAGE, or GAGE coding sequence, as will be seen by comparing it to the sequence of any of these genes as described in the cited references.

Figure 2B:
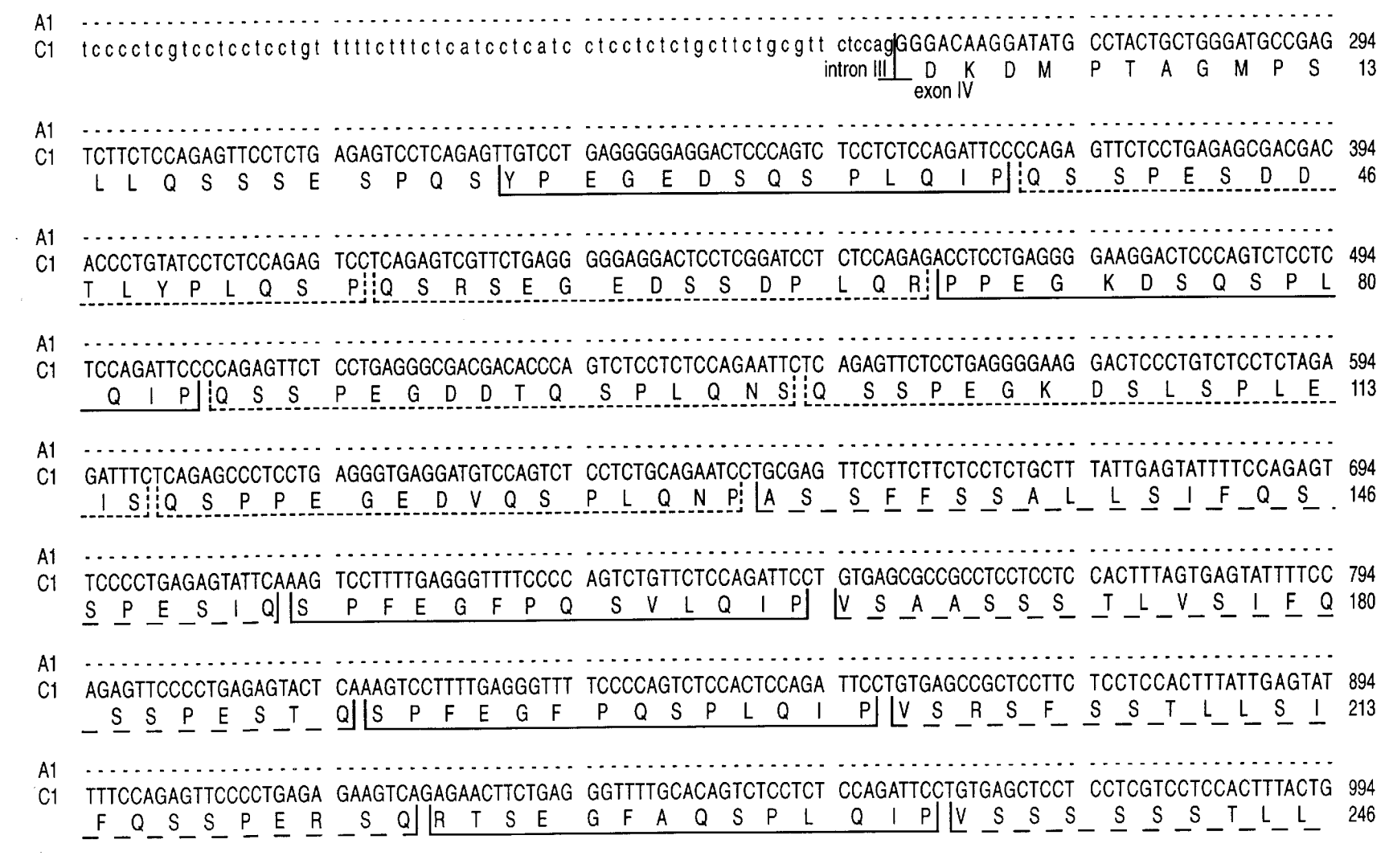
Figure 2C:
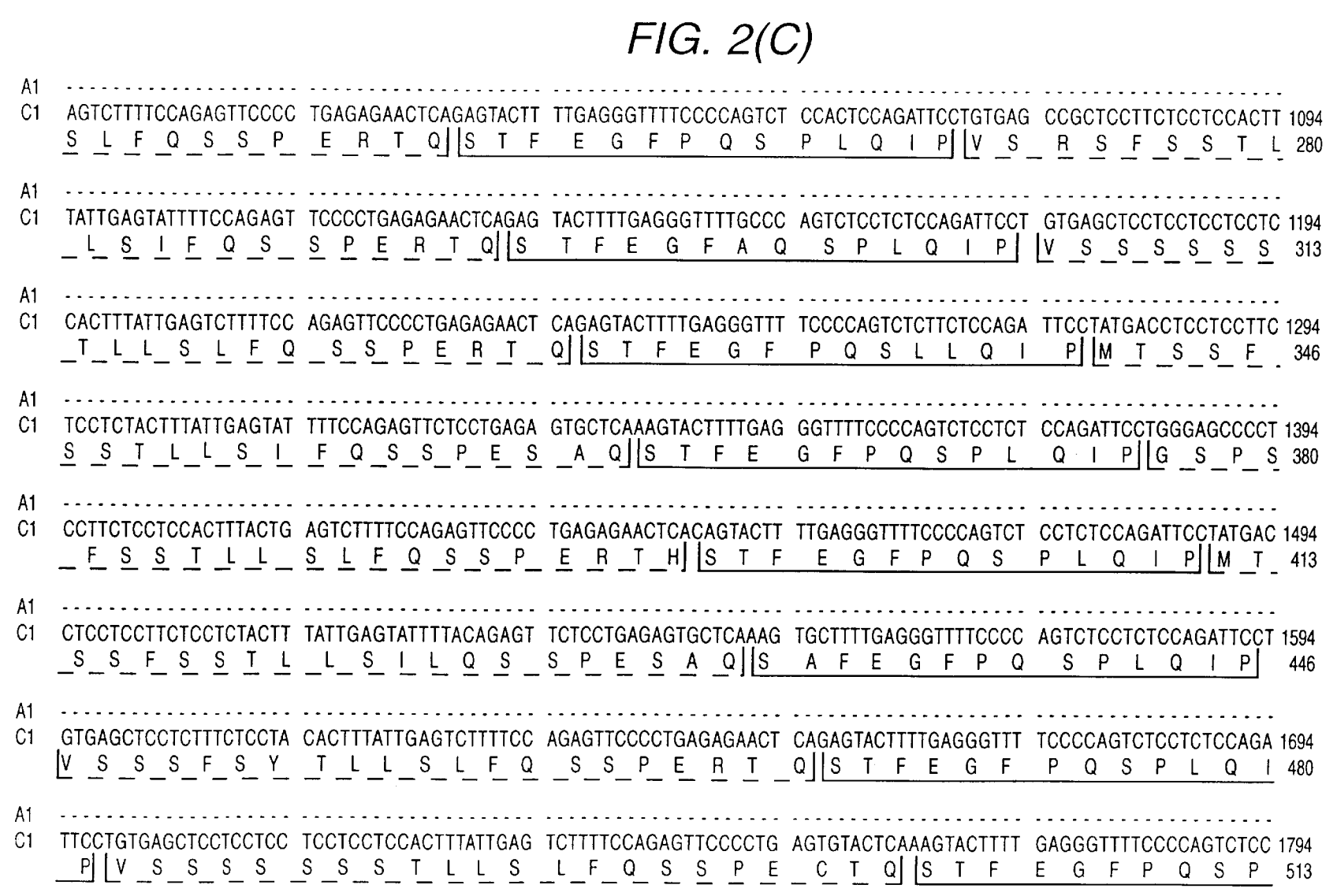
Figure 2E:
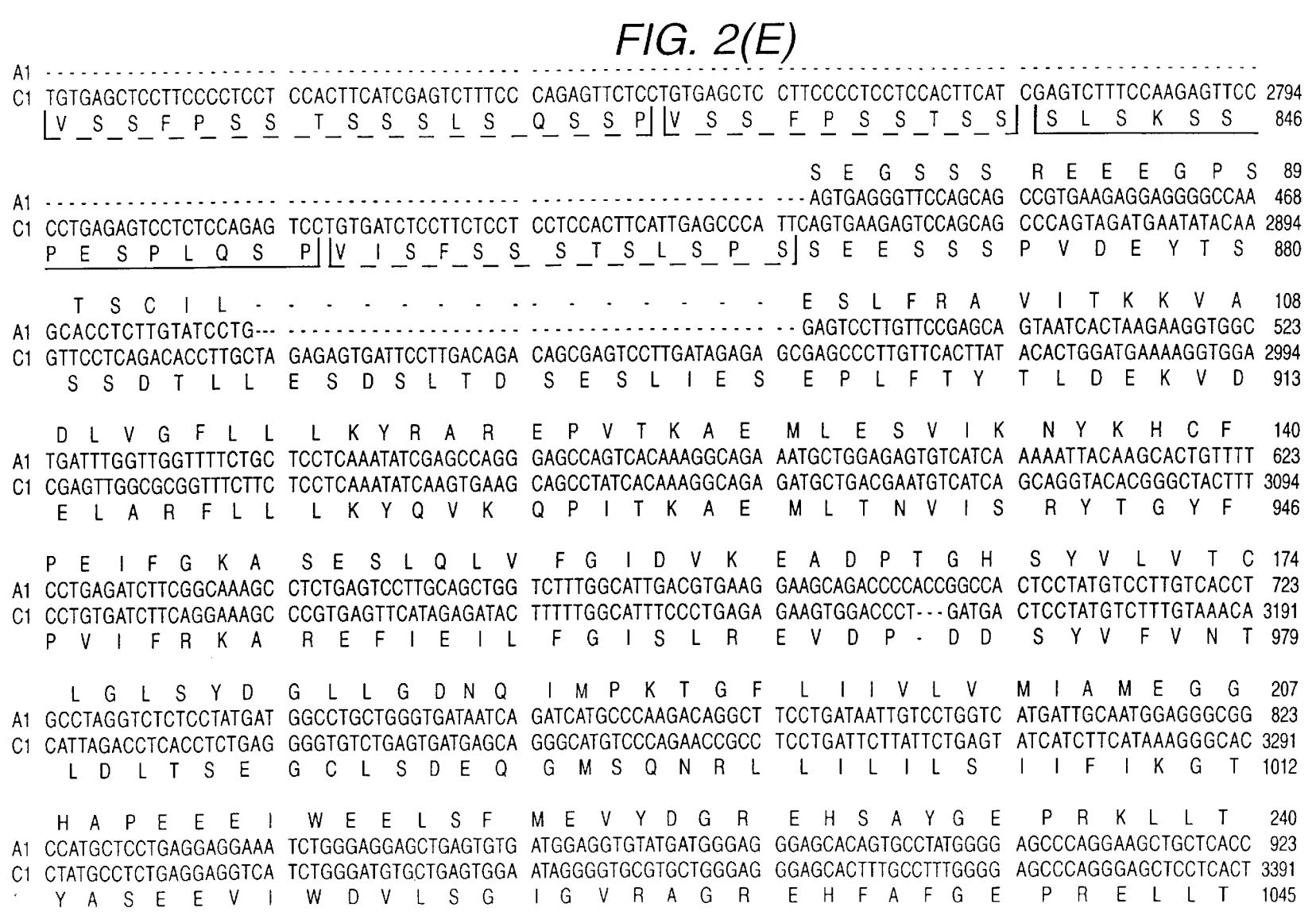

Also a part of the invention are those nucleic acid molecules having the nucleotide sequence of nt 1–2815 and nt 2816–4225 of SEQ ID NO:9. Another embodiment of this invention is a nucleic acid molecule, which codes for a tumor rejection antigen precursor and hybridizes to a nucleic acid molecule having the nucleotide sequence 1–2815 of SEQ ID NO:9 but does not hybridize to nucleic acid molecules having the nucleotide sequence of SEQ ID NO:8, i.e., the MAGE-A1 nucleotide sequence as set forth in FIG. 2, under stringent conditions. The term "stringent conditions" as used herein, refers to hybridization in 5x SSC, 0.1% SDS, 5x Denhardt's reagent at 65° C., overnight, followed by two washes at room temperature for 20 minutes, in 2x SSC and 0.1% SDS, and one wash for 20 minutes in 2x SSC and 0.1% SDS at 65° C., and one wash in 0.2x SSC, 0.1% SDS at 65° C. There are other conditions, reagents, and so forth which can be used, which result in the same or higher degree of stringency. The skilled artisan will be familiar with such conditions and, thus, they are not given here.

The widespread distribution in the expression of MAGE-C1 in tumor cells and not in normal cells, demonstrates that the isolated nucleic acid molecule can be used as a diagnostic probe to determine the presence of abnormal, e.g., tumor, cells which express MAGE-C1 related sequences. The identification of seminoma was 100% (Table 2) so on a very basic level, the isolated nucleic acid molecules may be used to determine whether or not seminoma is present. Note that there are many ways available to the skilled artisan to confirm that a tumor sample is a seminoma, and these need not be reiterated here.

It will also be seen from the examples that the invention embraces the use of the sequences in expression vectors, which may be used to transform or to transfect host cells and cell lines, be these prokaryotic (e.g., E. coli), or eukaryotic (e.g., CHO or COS cells). The expression vectors require that the pertinent sequence, i.e., those described supra, be operably linked to a promoter. The expression vector may include e.g., a sequence encoding one or more HLA molecules. In a situation where the vector contains both coding sequences, it can be used to transform or transfect a cell which does not normally express either one. The tumor rejection antigen precursor coding sequence may be used alone, when, e.g., the host cell already expresses HLA-molecules. The particular host cell which is suitable for expressing the sequences described herein include, e.g. prokaryotic or eukaryotic cells, such as E. coli, CHO, COS cells or insect cells.

Another aspect of this invention is the isolation of a genomic DNA (gDNA) which encodes a protein having the amino acid sequence encoded by a nucleic acid molecule having SEQ ID NO:9. Such a gDNA may be identified and isolated using well known methods in the art. For example MAGE-C1 specific probes derived from SEQ ID NO:9 may be used to screen a genomic DNA library prepared from, e.g., LB373-MEL cells. Those of ordinary skill in the art will be able to determine from sequence analysis those sequences which are specific for MAGE-C1. It is also possible using techniques well known in the art to determine the chromosome where such a gDNA is located, see. e.g., PCT/US95/02203 incorporated in its entirety by reference.

Another embodiment of this invention is an expression kit, which enables the artisan to prepare a desired expression vector or vectors. Such expression kits include at least separate portions of each of the previously discussed coding sequences; e.g., a vector ,such as a bacterial plasmid, a cosmid or a viral vector which comprises a promoter (DePlaen et al., P.N.A.S 85:2274–2278 (1988), Grosveld et al., Gene 10:6715–6732 (1982), and Bates et al., Gene 26:137–146 (1983) incorporated in their entirety by reference), any of the HLA coding sequences, such as those set forth in Zemmour and Parham, Immunogenetics 37:239–250 (1993), a MAGE-C1 coding sequence, or both an HLA and a MAGE-C1 coding sequence. Other components, such as e.g., resistance markers, enhancers or inducible promoters which are known in the art may be added, as desired.

To distinguish the nucleic acid molecules and the TRAPs and TRAs of this invention from the previously described MAGE, BAGE, and GAGE materials, the invention shall be referred to as the MAGE-C1 gene and MAGE-C1 TRAP and TRAs. Hence, whenever MAGE-C1 is used herein, it refers to the tumor rejection antigen precursors, and their derived TRAs, which are encoded for by the previously unknown nucleic acid sequence. "MAGE-C1 coding sequence" and similar terms, are used to describe the nucleic acid molecules themselves.

The invention as described herein has a number of uses, some of which are described herein. First, the invention permits the artisan to diagnose a disorder characterized by expression of the MAGE-C1 messenger RNAs and the MAGE-C1 TRAP and TRAs. The methods involve determining the expression of mRNAs from the MAGE-C1 nucleic acid molecules and related molecules, and/or the presence of TRAs derived from the TRAP encoded by MAGE-C1 and related nucleic acid molecules. In the former situation, such determinations can be carried out via any standard nucleic acid determination assay, including the polymerase chain reaction, or assaying with labeled hybridization probes. In the latter situation, TRAP and TRA may be detected by assaying for the TRAP or TRA alone or assaying for complexes of TRA and HLA, using binding partners such as, e.g., as antibodies. Another embodiment of this invention is to detect the presence of cytolytic T cells specific for complexes of an HLA molecule and a peptide derived from the protein encoded by the isolated nucleic acid molecule of claim 1 in a CTL-containing sample, comprising contacting said sample with cells, which present said complexes on their surface, and determining (I) proliferation of cytolytic T cells, or (ii) lysis of cells presenting said complexes, as a determination of said cytolytic T cells in said sample. CTL proliferation may be detected by assaying TNF release or the release of a radiolabelled substance, such as $^{51}Cr$, as described, e.g., in PCT/US95/02203 incorporated in its entirety by reference.

The isolation of this MAGE-C1 nucleic acid molecule also makes it possible to isolate the TRAP molecules themselves, especially TRAP molecules consisting of the amino acid sequence encoded by SEQ ID NO:9. The isolation of the MAGE-CL nucleic acid molecule also makes it possible to identify TRAs that are unique to MAGE-C1 discussed in more detail infra.

Further, the polypeptide having the amino acid sequence encoded by nucleotide sequence 1–4225 of SEQ ID NO:9 and polypeptides derived these from are also part of this invention. These polypeptides alone or in combination with other polypeptides, may be combined with materials such as adjuvants which are well-known in the art see, e.g. U.S. Pat. No. 5,057,540 to Kensil et al., incorporated by reference or PCT application PCT/US92/03579 to Scott et al., also incorporated by reference to produce vaccines which will be useful in treating disorders characterized by expression of the molecules.

In addition, vaccines can be prepared from cells, such as non-proliferative cancer cells, non-proliferative transfectants, etcetera, which present the TRA/HLA complexes on their surface. In all cases where cells are used as a vaccine, the cells may be transfectants having been transfected with coding sequences for one or both of the components necessary to provide a CTL response, i.e., TRAP, TRA, and HLA molecules using techniques which are well-known in the art see e.g., PCT/US95/02203 and Zemmour supra for sequence of various HLA molecules. Alternatively, the cells may express both HLA and TRAP/TRA molecules without transfection. Further, the TRAP molecules, their associated TRAs, as well as complexes of TRA and HLA, may be used to produce antibodies, using standard techniques well known in the art.

When "disorder" is used herein, it refers to any pathological condition where the tumor rejection antigen precursor is expressed. An example of such a disorder is cancer, seminoma in particular.

Therapeutic approaches based upon the disclosure herein are premised on a response by a subject's immune system, leading to lysis of HLA/TRA presenting cells. One such approach is the administration of CTLs which are specific to an HLA/TRA complex to a subject having abnormal cells of the phenotype at issue. It is within the skill of the artisan to develop such CTLs in vitro see, e.g., Herin et al. supra. For example, a sample of cells, such as blood cells, are contacted to a target cell presenting an HLA/TRA complex and capable of provoking a specific CTL to proliferate. The target cell can be a transfectant, such as a COS cell transfected with and expressing a particular HLA and TRAP as described supra. These transfectants present the desired complex on their surface and, when combined with a CTL of interest, stimulate its proliferation. COS cells, such as those used herein are widely available, as are other suitable host cells including but not being limited to, CHO cells, *Spodopitera furjiperda, E. Coli,* Bacillus, and so forth.

One therapeutic methodology is referred to as adoptive transfer (Greenberg, J. Immunol. 136(5):1917 (1986); Riddel et al., Science 257:238 (Jul. 10, 1992); Lynch et al., Eur. J. Immunol. 21:1403–1410 (1991); Kast et al., Cell 59:603–614 (Nov. 17, 1989). In adoptive transfer, cells presenting the desired HLA/TRA complex are combined with CTLs leading to proliferation of the CTLs which are specific for that complex. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the relevant HLA/TRA complex. This can be determined easily, as the art is very familiar with methods for identifying cells which present a particular HLA molecule, as well as how to identify cells expressing DNA of the pertinent sequences, in this case a MAGE-C1 and related sequence. If the abnormal cells of the patient present the relevant HLA/TRA complex then the patient is an appropriate candidate for the therapeutic approaches set forth supra.

Adoptive transfer is not the only form of therapy that is available in accordance with the invention. CTLs can also be provoked in vivo, using a number of approaches. One approach, i.e., the use of non-proliferative cells expressing the complex as a vaccine, has been elaborated upon supra. The cells used in this approach may be those that normally express the complex, such as irradiated seminoma cells or irradiated cells transfected with one or both of the genes necessary for presentation of the complex. Chen et al., Proc. Natl. Acad. Sci. USA 88:110–114 (January, 1991) exemplifies this approach, showing the use of transfected cells expressing HPV E7 peptides in a therapeutic regime. Various cell types may be used.

Similarly, vectors, such as viral or bacterial vectors, carrying a nucleic acid molecule encoding either an HLA or a TRAP or TRA, or combination thereof, may be used. In these systems, the nucleic acid molecule is carried by, e.g. a Vaccinia virus or the bacteria BCG, which "infect" host cells. The infected cells present the HLA/TRA complex and are recognized by autologous CTLs, which then proliferate.

CTLs can also be provoked in vivo by combining the TRA or the TRAP itself with an adjuvant to facilitate incorporation into HLA presenting cells. The cells present the HLA/peptide complex of interest by further processing the TRAP to yield the peptide partner of the HLA molecule. Alternatively, the cells may present the TRA without the need for further processing. See, e.g., Braciale, T. J. and Braciale, V. L., Immunology Today, 12:124–129 (1991); T. Elliot, Immunology Today, 12:386–388 (1991), and: Madelboim et al., Nature, 369:67–71 (1994).

Also a feature of this invention are isolated peptides derived from the MAGE-C1 TRAP, which conform to the rules for presentation by MHC molecules. For example, in PCT application No. PCT/US93/07421, incorporated by reference herein, several motifs are described as being associated with different MHC molecules. These motifs, incorporated by reference herein, as well as those taught by, e.g. Falk et al., Nature 351:290–296 (1991); Engelhard, Ann. Rev. Immunol 12:181–207 (1994); Ruppert et al., Cell 74:929–937 (1993); Rötzschke et al., Nature 348:252–254 (1990); Bjorkman et al., Nature 329:512–518 (1987) and Traversari et al., J. Exp. Med. 176:1453–1457 (1992) all of which are incorporated by reference, serve as a basis for identifying appropriate peptides obtainable or derivable from the MAGE-C1 amino acid sequence and the nucleotide sequence which encodes the protein. In another aspect of the invention these peptides may be used alone, or in mixtures, to stimulate CTL proliferation. These peptides are also useful in vaccines.

It is well established that the blood of individuals afflicted with tumors frequently contains cytolytic T cells ("CTLs") which recognize complexes of MHC molecules and presented peptides. See e.g., Robbins et al., Canc. Res. 54:3124–3126 (1994); Topolian et al., J. Immunol. 142:3714–3725 (1989); Coulie et al., Int. J. Cancer 50:289–297 (1992), all of which are incorporated by reference. Also, note Kawakami et al., J. Exp. Med. 180:347–352 (1994); Hom et al., J. Immunother. 10:153–164 (1991), Darrow et al, J. Immunol. 142(9):3329–3335 (1989); Slovin et al., J. Immunol. 137(9):3042–3048 (1986), all of which are incorporated by reference. These papers all establish the usefulness of a CTL proliferation assay to diagnose possible cancer.

In general, a patient will only have CTLs which recognize and proliferate in response to contacting target cells presenting particular complexes of TRA and HLA only if at least some of the patient's own cells are also expressing that particular complex. If one takes a peripheral blood lymphocyte (PBL) containing sample from a patient suspected of having abnormal cells, e.g., tumor cells, and contacts that CTL-containing sample with a target cell which presents complexes of a relevant MHC molecule and a MAGE-C1 derived peptide one will only see proliferation of CTLs which are specific for that complex. Thus proliferation of CTLs in the patient's PBL sample will indicate that the patient possibly has tumor cells which express that particular HLA/TRA complex. The target cells may be cells which normally present the MHC molecule in question or may be cells which have been transfected with an HLA coding sequence. The target cells may conceivably be tumor cells, or normal cells.

One embodiment of the invention involves mixing a target cell sample with (1) a peptide or mix of peptides which are derived from a MAGE-C1 TRAP and presented by the target cell MHC molecules and (2) a PBL sample of the subject under evaluation. The mixture is then tested for CTL proliferation. Various methods of determining CTL proliferation are known in the art, e.g., TNF release assays, and $^{51}$Cr release assays see e.g. PCT/US95/02203.

The peptide or peptides of this invention may also be combined with one or more adjuvants to stimulate a more pronounced CTL response. Exemplary of such adjuvants are saponins and their derivatives, such as those disclosed by U.S. Pat. No. 5,057,540 to Kensil et al., incorporated by reference or PCT application PCT/US92/03579 to Scott et al. also incorporated by reference. Of course, standard adjuvants, such as Freund's complete adjuvant, or Freund's incomplete adjuvant, may also be used.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

EXAMPLE 1

Generation of Difference Products (DP) for Tumor LB373-MEL and Testis

A cDNA library enriched for sequences present only in the cell type of interest, a "tester" cell, and not present in another cell type, a "driver" cell, was generated essentially as described by Hubank and Schatz, Nuc. Acids. Res. 22:5640–5648 (1994) incorporated herein in its entirety by reference. Briefly, total RNA was prepared from tester cells and driver cells. Herein the tester cells were melanoma cells LB373-MEL and the driver cells were normal skin cells. Poly-A+RNA was isolated from total RNA using oligo-dT columns using techniques well known in the art. The poly-A+RNA was then reverse transcribed to produce cDNA. The cDNA was digested with restriction enzyme Dpnll, which cuts DNA at GATC sites, to generate short fragments of double stranded DNA with 5'-GATC overhangs. Double-stranded DNA adapters with a 5'-GATC overhangs (R-Bgl adaptor which is composed of annealed R-Bgl-12 and R-Bgl 24 oligonucleotide SEQ ID NO:2 and SEQ ID NO:2A respectively) were ligated to the Dpnll digested cDNA prepared from the tester and driver cells. The adaptor-ligated cDNA was subsequently amplified by the well-known polymerase chain reaction (PCR). The amplified product is a "representation" of the tester and the driver, respectively.

Both tester and driver representations were digested with Dpnll. Digested tester was ligated to new adaptor molecules (J-Bgl adaptor which is composed of annealed J-Bgl-12 and J-Bgl-24 oligonucleotide SEQ ID NO:3 and SEQ ID NO:3A respectively). A first round of subtractive hybridization was then performed by mixing in 100/1 proportions the digested driver cDNA with the digested tester cDNA ligated to the J-Bgl adapters. The mixed driver and tester cDNA sample was denatured at 98° C. for 5 min and then incubated at 67° C. for 20 hours to rehybridize the denatured sample. This resulted in a mixture of hybrid double-stranded cDNAs. The hybrid cDNAs were of three types. One hybrid type constituted two tester cDNA molecules which represented nucleotide sequences unique to the tester cells, a second hybrid type constituted two driver cDNA molecules and a third hybrid type constituted one tester cDNA molecule and one driver cDNA molecule. After hybridization, the sample was PCR amplified using a single stranded J-Bgl adaptor, J-Bgl-24 SEQ ID NO:3A. Hybrid cDNAs composed of two driver cDNA molecules were not amplified, because they did not comprise the J-Bgl adaptor. Hybrid cDNAs constituted by one tester cDNA molecule and one driver cDNA molecule were only amplified linearly. Only double stranded cDNA consisting of two tester cDNA molecules were amplified exponentially.

After 10 cycles of PCR amplification as described supra, the sample was treated with Mung Bean Nuclease (which digests specifically the single stranded DNA produced by the linear amplification), then subjected to 18 additional PCR cycles. The resulting enriched product was designated difference product 1 (DP1). DP1-Testis [-HLLK] and DP1-LB373 [-skin] were both generated.

J-Bgl adapters on DP1 were changed for N-Bgl-12/24 adapters (N-Bgl-12: 5'GATCTTCCCTCG-3'; N-Bgl-24:

5'-AGGCAACTGTGCTATCCGAGGGAA-3'), i.e., annealed N-Bgl-12 and N-Bgl-24 oligonucleotides, SEQ ID NO:4 and SEQ ID NO:4A and the process of subtractive hybridization and selective amplification repeated to generate the second difference products (except that annealing and extension in PCR reactions were performed at 72° C.). Tester to driver ratios were of 1/800 to generate DP2.Testis (-HLLK), but of 1/100 to generate DP2.LB373(-skin). A third difference product DP3.Testis(-HLLK) was generated by repeating the process with J-Bgl ligated DP2.Testis(-HLLK) as tester and HLLK representation as driver, with final amplification performed of 22 cycles.

EXAMPLE 2

Search for Sequences Common to DP2.LB373[-Skin] and DP3.Testis[HLLK]

Many known tumor antigens are encoded by genes that are expressed only in tumors and in testis. By searching for sequences that were common to both DP3.Testis[-HLLK] (representing nucleic acid sequences unique to testis cells) and DP2.LB373[-skin] (representing nucleic acid sequences unique to melanoma cells), as described supra nucleic acid sequences were identified that were expressed only in testis and tumor cells that encode previously unidentified tumor antigens.

To clone DP3.Testis[-HLLK] DNA, DP3.Testis[-HLLK] was digested with DpnII and the digested DNA was ligated to BamHI digests of the commercially available plasmid pTZ18R. The bacteria, DH5αF'IQ (commercially available), was electroporated with ligated DNA. The electroporated bacteria were selected and screened by colony hybridization with a probe produced by labeling DP2.LB373 [-skin] with random primers, Klenow DNA polymerase and α-$^{32}$P-dCTP.

Plasmids from transformants which hybridized to the DP2.LB373[-skin] probe were isolated and their inserts analyzed. One clone containing a 283 bp insert was purified and sequenced using techniques well known in the art. The sequence of the 283 bp insert shared partial homology with the MAGE gene family. Maximum homology (74%) was obtained with a 147 nucleotide sequence, corresponding to nucleotides 9895 to 10041 of MAGE-4a cDNA, as predicted from the MAGE 4a genomic DNA (Genbank accession no. U 10687), incorporated herein by reference These data suggested that the 283 bp insert was a portion of a previously unidentified MAGE family member. This family member was designated MAGE-C1.

EXAMPLE 3

Complete MAGE-C1 cDNA

To obtain the complete MAGE-C1 cDNA, a cDNA library, prepared from LB373-MEL RNA and subcloned into pcDNAI/Amp, was screened. The cDNA library was prepared as follows.

Total RNA was extracted from LB373-MEL cells by the guanidine-isothiocyanate procedure (Davis L. G., M. D., Dibner and J. F. Battery, Basic Methods in Molecular Biology, Elsevier, N.Y., pp. 130–135 (1986)). Poly-A+RNA was purified on oligo-dT columns (Pharmacia) and converted to cDNA using an oligo-dT (NotI, EcoRI) primer SEQ ID NO:5. The cDNA was ligated to BstXI adaptors (SEQ ID NO:6), digested with NotI and ligated with BstXI and NotI digested commercially available expression vector pcDNAI/Amp using methods well known in the art. Top 10F' *Escherichia coli* bacteria were electroporated with the ligated recombinant plasmids and transformants selected with ampicillin (50 μg/ml). The library was screened with a $^{32}$P-radiolabelled probe derived from the 283 bp insert isolated supra.

Bacterial transformants were screened for MAGE-C1 sequences by using methods well-known in the art. Briefly, approximately 140,000 bacteria were plated on nylon membrane filters. Duplicate nylon membrane filters were made and treated to denature and fix the bacterial DNA. A 168 bp MAGE-C1 specific probe was generated by RT-PCR (reverse transcription-PCR) using LB373-MEL RNA as template, and MAGE-C1 specific primers, i.e., sense primer SL26: 5'CCAGTAGATGAATATACAAGTT-3' which corresponds to nucleotides (nt) 2766 to nt 2787 of SEQ ID NO:1 and antisense primer SL27: 5'-GATAGGCTGCTTCACTT-3', which is the complementary sequence of nt 2917 to nt 2933 of SEQ ID NO:1. This 168 bp MAGE-C1 PCR product, which corresponds to nt 2766 to 2933 of SEQ ID NO:1, was purified on a sepharose CL-6B column, then labeled using random primers, Klenow DNA polymerase and α-$^{32}$P-dCTP as described supra (Example 3). The treated duplicate membrane filters were hybridized with the MAGE-C1 specific probe (500,000 cpm/ml; overnight incubation at 65° C. in 5X SSC, 0.1% SDS 5X Denhardt's reagent), then washed in stringent conditions, and autoradiographed for 70 hours at room temperature. Stringent conditions as described herein refers to 0.1X to 0.5X SSC, 0.1% SDS at 65° C. for 20 min. Two colonies were identified which hybridized to the MAGE-C1 probe. The colonies were purified and screened once again to verify that they hybridized to the probe. Plasmids were isolated from these colonies and their inserts sequenced and analyzed using methods which were well-known in the art. One clone was selected and the MAGE-C1 cDNA inserted analyzed in detail. The analyzed clone contained a MAGE-C1 cDNA molecule 4031 bp long (FIG. 1) SEQ ID NO:1. An open reading frame (ORF) runs almost through the entire cDNA with a first ATG, located at nt 257, in accordance with the known Kozak rule, and a stop codon at nt 3473. The ORF encodes a putative protein of 1072 amino acids.

Alignment with the MAGE-A1 cDNA revealed significant homologies between the MAGE-C1 cDNA (SEQ ID NO:1) and MAGE-A1 exons 2 and 3. The open reading frame of MAGE-C1, however, is about 2 kb longer than that of MAGE A1, most of the difference being accounted for by a large repetitive sequence.

EXAMPLE 4

MAGE-C1 Expression

Sense primer SL33 (5'-CGGAGGGAGGAGACTTA-3') nt 18–34 of SEQ ID NO:1 and antisense primer SL34 (5'-TTAAGGTGGTGCTCTAGG-3') which is complementary to nt 200–217 of SEQ ID NO:1 are shown in FIG. 1. These primers are located in different exons, as determined by the different sizes of PCR products from cDNAs (202 bp) or genomic DNAs (approximately 1.1 kb) prepared from normal tissue and tumor cells. The expression pattern of the MAGE-C1 messenger RNA was determined by standard RT-PCR analysis of normal tissue and tumor samples. The data indicate that MAGE-C1 expression is not detected in the normal tissues tested (Table 1), with the exception of testis. Among tumor cell samples, MAGE-C1 expression is frequently detected in melanoma (46%), seminoma (100%), bladder transitional-cell carcinoma (18%), breast carcinoma (16%) and non-small cell lung carcinoma (16%). It is also detected in a significant fraction of sarcoma, head and neck carcinoma, and prostate adenocarcinoma.

EXAMPLE 5

Northern Blot Analysis

10 µg total RNA extracted by the guanidine-isothiocyanate procedure (Davis et al., *Basic Methods in Molecular Biology*, Elsevier, N.Y., pp. 130–135 (1986) were separated by formaldehyde agarose gel electrophoresis, transferred to a nylon membrane by capillary transfer and fixed by UV irradiation. Hybridization to the MAGE-C1 1.3 kb XbaI-EcoRI probe corresponding to nucleotide 589 to 1904 of SEQ. ID. NO:1 (radiolabeled with [$\alpha$-$^{32}$P]dCTP) was performed overnight at 60° C. in 10% dextran sulfate, 1M NaCl, 1% SDS and 100 µg/ml denatured salmon sperm DNA. The membrane was washed consecutively in 2x SSC, 0.1% SDS for 20 min at room temperature, in 2x SSC, 0.1% SDS for 20 min at 60° C., and finally in 0.2x SSC, 0.1% SDS for 5 min at 60° C. Autoradiography was performed for 7 days using BioMax MS film (Kodak). The same membrane was hybridized to a β-actin specific probe in identical conditions, except washing was performed twice for 10 min in 2x SSC at room temperature and autoradiography performed overnight. A MAGE-C1 messenger species migrating around 4 kb in total RNA from normal testis and some tumor cell lines was observed. No MAGE-C1 messenger species were detected in total RNA from normal lung.

EXAMPLE 6

Structure of the MAGE-C1 cDNA

Sequencing and alignment of SEQ ID NO:1 (FIG. 2 and FIG. 3) revealed that the MAGE-C1 cDNA is homologous to MAGE-A1 (Van der Bruggen et al., Science 254:1643 (1991)) only in its 3' third. Except for another short stretch of homology to the second exon of MAGE-A1, MAGE-C1 is composed of sequences unrelated to MAGE family or to any sequence reported in databanks. Compared to other MAGE cDNAs, MAGE-C1 contains an approximately 2.4 kb insertion represented in FIG. 3 by a large hatched box, which comprises 3 types of tandemly repeated sequences: 42 bp-repeats, 63 bp-repeats, and 48 bp-repeats.

EXAMPLE 7

Southern Blot Analysis

Southern blots prepared with several genomic DNAs from melanoma cell lines LB373-MEL, SK29-MEL, and LB33.A-1, (Coulie et al. *J. Exp. Med.* 180:35–42 (1994); Coulie et al., *Proc. Natl. Acad. Sci. USA* 92:7976–7980 (1995); Lehmann et al. *Eur. J. Immunol.* 25:340–347 (1995)), were hybridized with a 1.3 kb XbaI-EcoRI cDNA probe derived from SEQ ID NO:1, which contains most of the insertion that distinguishes cDNA clone MAGE-C1 from other MAGE cDNAs. Ten µg genomic DNA digested with a restriction enzyme were separated by agarose gel electrophoresis, transferred to nylon membranes by the capillary transfer method and fixed by UV irradiation as described (Sambrook et al., *Molecular Cloning, A Laboratory Manual*, N.Y. Cold Spring Harbor Laboratory Press, pp. 9.31–9.58, incorporated here by reference). Hybridization to the [$\alpha$-$^{32}$P]dCTP radiolabeled MAGE-C1 1.3 kb XbaI-EcoRI probe was performed in 5x SSC, 5x Denhardt's, 0.1% SDS and 100 µg/ml denatured salmon sperm DNA for 12 to 24 hours at 68° C. Membranes were washed consecutively in 2x SSC, 0.1% SDS for 20 min at room temperature, in 2x SSC, 0.1% SDS for 20 min at 68° C., and in 0.2x SSC, 0.1% SDS for 20 at 68° C. Autoradiography was performed for 3 days using BioMax MS film (Kodak).

A single hybridizing band was present in DNA from the SK29 melanoma line digested with 5 distinct restriction enzymes, suggesting that MAGE-C1 is the only gene of its type in the MAGE-family. However, PstI digested DNAs isolated from peripheral blood lymphocytes of 11 male patients contain each a unique MAGE-C1 band, but of different sizes, suggesting the existence of allelic polymorphism in gene MAGE-C1. EcoRI digested DNAs from LB373-MEL and LB33-MEL.A-1 contain a unique MAGE-C1 band of identical size (see FIG. 3 for positions of probe and restriction sites).

EXAMPLE 8

Isolation of MAGE-CL Gene

To isolate the MAGE-C1 gene, a cosmid library prepared with genomic DNA from melanoma line LB33-MEL.A-1 was screened. Genomic DNA from melanoma line LB33-MEL.A-1 was partially digested with Mbo1 and ligated to cosmid arms of vector c2RB as described (Lurquin, C. et al., Cell 58:293–303 (1989)) incorporated by reference]. The ligated DNA was packaged into λ phage heads (GIGAPACK, Strategene) and titrated on *Escherichia coli* ED8767. The library was represented by 40 groups of 70,000 independent cosmids. Each group was used to infect Ed8767 bacteria, and amplified in LB medium containing 50 µg/ml ampicillin. Aliquots of 16 hour-cultures were frozen, others were titrated to evaluate the amplification of the library ($10^5$x), the remainder of the cultures was further amplified and used to isolate total cosmid DNA, as described (De Plaen, *Immunology Methods Manual*, Academic Press Ltd., 9.9:691–718 (1997) incorporated by reference).

DNA extracted from 16 groups of approximately 70,000 independent cosmids was submitted to PCR amplification with MAGE-C1 primers. Twelve groups were found positive, and one of these was screened by colony hybridization with the XbaI-EcoRI probe. A positive cosmid, C7.2, was identified. Restriction analysis and Southern blot revealed that this cosmid contained an approximately 42 kb insert carrying 4 EcoRI fragments of 1, 1.4, 1.6, and 2 kb, respectively, and one BamHI fragment of 2 kb, which hybridized with a probe corresponding to the entire MAGE-C1 cDNA clone (SEQ ID NO:1). Those 5 fragments were subcloned in phagemid pTZ19R and their nucleotide sequence was determined. Comparison of these sequences with the cDNA clone showed that MAGE-C1 is composed of four exons (FIG. 3) A 3,426 base pair open reading frame starts with an ATG located at the end of exon III, and runs through most part of exon IV. All repeated motifs are included in the latter but the length of this repetitive region was longer in the gDNA clone as compared to that found in the cDNA clone. Although the cDNA and genomic clones came from libraries of different origins (sublines of LB373-MEL and LB33-MEL.A-1 respectively), allelic variation could hardly explain this discrepancy, as demonstrated by Southern blot analysis with the XbaI-EcoRI probe. To confirm Southern analysis results, genomic DNA from both cell lines was amplified by PCR with primers SL38 (5'-GGCGACGACACCCAGT-3') corresponding to nt 521 to 536 of SEQ ID NO:1 and SL43 (5'-AGGAAAGTAGAGAGGAGACAT-3') corresponding to nt 1862 to 1882 of SEQ ID NO:1 and products of identical sizes were obtained. Partial sequencing of these PCR products showed no difference at the nucleotide level between the two cell lines, excluding the presence of a splice site in LB373-MEL cells, that is absent in LB33-MEL cells.

To determine if reverse transcription artifacts accounted for the differing lengths of the repetitive regions in the gDNA and cDNA clones, cDNA obtained from reverse transcription of total RNA was amplified by PCR using primers SL38 and SL43.

The Transcription in vitro Systems (Promega) was used to produce MAGE-C1 RNA for the PCR amplification and cloning of MAGE-C1 repetitive region from cDNA. One μg HindIII digested pcDNAI/Amp containing MAGE-C1 cDNA clone was diluted to a final volume of 20 μl with 4 μl 5x SP6 buffer, 1 μl each NTP at 10 mM, 2 μl dithiotreitol at 0.1M, 0.5 μl (20 Units) RNase inhibitor and 1 μl (15 units) SP6 RNA polymerase. A control reaction was set up where 5 μl [α-$^{32}$P]CTP (3000Ci/mmol) were added to a mixture identical to the transcription mixture described above, except that only 2.4 μl of 0.1 mM CTP were used. The reactions were incubated at 37° C. for 1 hour. One μl (1U) RQ1 DNase was added to the mixtures which were incubated again for 1 hour at 37° C. One tenth of the radiolabeled RNA was analyzed by electrophoresis on a formaldehyde agarose gel, the gel was dried and autoradiographed to confirm that only full length products were obtained. Non-radioactive RNA was phenol extracted, ethanol precipitated, and resuspended in 10 μl water. One μl RNA solution was reverse transcribed in the same conditions as total RNA (Weynants et al. Int. J. Cancer 56:826–829 (1994)), incorporated herein by reference). To exclude contamination with plasmid DNA, a control reaction was included where no MoMLV reverse transcriptase was added. 1/40 of the completed reactions were engaged in 37 PCR cycles with SL38 sense primer and SL43 anti-sense primer. PCR products were fractionated by agarose gel electrophoresis. No detectable product were detected in control reactions.

Sense primer SL38 (5'-GGCGACGACACCCAGT-3') corresponding to nt 521 to 536 of SEQ ID NO:1 and anti-sense primer SL43 (5'AGGAAAGTAGAGAGGAGACAT-3') corresponding to nt 1862 to 1882 of SEQ ID NO:1 were used to amplify cDNA (1/40 of reverse transcription product from 2 μg total RNA) or 500 ng genomic DNA from melanoma lines LB373-MEL and LB-33-MEL.A-1. PCR was performed in 50 μl final volume, with 5 μl 10x DynaZyme buffer, 1 μl each of 10 mM dNTP, 25 pmoles each primer and 2 units DynaZyme (FynnZymes Oy), for 30 (genomic DNA) or 37 (cDNA) cycles of 1 min at 94° C., 1 min at 65° C. and 2 min at 72° C.

PCR products were ligated to plasmid pCR3 using the Eukaryotic TA Cloning Kit (Invitrogen), and ligation products were electroporated in Top10F' bacteria. Multiple products were obtained, with sizes ranging from 1.6 to 0.35 kb. In contrast, a single product was obtained from genomic DNA amplified by PCR with primers SL38 and SL43. Multiple PCR products were also generated with template cDNA obtained from reverse transcription of a full length RNA transcribed in vitro from cDNA clone MAGE-C1 (SEQ ID NO:1). These results suggest reverse transcription artifacts are responsible for the discrepancy between genomic and cDNA clones, and that the natural mRNA species transcribed from the MAGE-C1 gene in melanoma line LB373-MEL must comprise the entire repetitive region as found in cosmid C7.2 as described supra. The sequence of a full-length cDNA of this natural mRNA is presented as SEQ ID NO:9.

The repetitive regions correspond to a total of 18 direct repeats of 14 amino-acids (aa), 17 repeats of 21-aa, and 16 repeats of 16 aa. Gene MAGE-C1 shares maximum overall homology with gene MAGE-A10. However, comparison and alignment are made in FIGS. 2 and 3 with MAGE-A1, the most well-characterized gene of the MAGE family. Exon 1 of gene MAGE-C1 has no homologous counterparts in other MAGEs, but it is noteworthy that one Spl and two Ets consensus binding sites immediately precede the first exon, as has been described in MAGE-1 (De Smet et al., Immunogenetics 42:282–290, (1995); De Smet et al., Proc. Natl. Acad. Sci. USA, 93:7149–7153, (1996)) and some MAGE-4 promoters (De Plaen submitted).

EXAMPLE 9

Chromosomal Localization of the MAGE-C1 Gene

Fluorescence in situ hybridization (FISH) experiments with cosmid C7.2 as a probe show that gene MAGE-C1 is located on the long arm of the X chromosome, on Xq27 band.

A human genomic cosmid probe for MAGE-C1 was used for fluorescence in situ hybridization. The entire MAGE-C1 cosmid clone was nick translated using Biotin-14 dATP and Biotin-14 dCTP (Gibco BRL) for fluorescence in situ hybridization and hybridized to normal human metaphase spreads in two independent experiments.

Chromosome preparations were obtained from phytohemagglutinin-stimulated normal peripheral blood lymphocytes cultured for 72 hours. To induce R-banding, some of the cultures were synchronized with thymidine after 48 hours, incubated at 37° C. and treated with 5'bromodeoxyuridine (BrdU) the next morning, during the final late S-phase, and harvested 6 hours later (Jacky, P. B., Raven Press, p. 89, (1991)). Cytogenetic harvests and slide preparations were performed using standard methods. The slides were stored at −80° C. before use.

Fluorescence in situ hybridization to metaphase chromosomes was performed as described by Pinkel et al. (Pinkel et al., Proc. Natl. Acad. Sci. USA, 83:2934–2938, (1986)). Briefly the biotin labeled probe (50–100 ng) was dissolved in hybridization mixture (50% formamide, 10% dextran sulfate, 2xSSC, 0.1 μg COT-1 DNA (Gibco BRL), 10 μg sheared salmon sperm DNA as carrier) and incubated for 60 min. at 37° C. to allow the COT-1 DNA to anneal to repetitive sequences in the probe. The probe mixture was then applied to the slide and co-denatured for 10 minutes at 80° C. on a slide warmer. Hybridization was allowed to proceed overnight in a humid chamber at 37° C. The slides were washed using the formamide-wash procedure as per the FITC-biotin detection kit and, when appropriate, the amplification protocol for dual color FISH (Oncor). Biotin-labeled probe detection was accomplished by incubation with the FITC-avidin conjugate and the digoxigenin-labeled chromosome X specific α-satellite repeat probe was detected using an anti-digoxigenin-rhodamine conjugate.

Chromosome identification was performed by simultaneous hybridization with a chromosome X-specific a-satellite repeat probe (Oncor) or by R-banding using 5-bromodeoxyuridine and mounting the slides in a modified antifade mounting solution of p-phenylenediamine (pH11) (Lemieux et al., Cytogenet. Cell Genet., 59:311–312 (1992)) containing 0.01 μg/ml propidium iodide as counterstain to produce an R-banding pattern. Slides were examined and photographed using a Zeiss Axiophot microscope and appropriate UV-filter combinations. The 35 mm slides were scanned using a Nikon Coolscan, processed using Adobe Photoshop 4.0 and printed using a Fujix Pictrography 3000.

The chromosomal localization of the human MAGE-C1 locus was initially obtained by somatic cell hybrid mapping in experiments not described here and was independently confirmed and refined by fluorescence in situ hybridization as described, supra. In these experiments, 47 R-banded metaphase spreads from normal lymphocytes were examined for specific signals of hybridization. Signals were considered to be specific only if they were detected on each chromatid of a single chromosome. Specific signals were seen in 15 of the 47 metaphases examined (32%). In each case the hybridization signals were located in the distal portion of the X chromosome. The R-banding pattern chromosomes allowed a more specific localization of the MAGE-C1 locus to Xq27-q28.

Interestingly, other members of the MAGE family have also been localized to both the long and short arms of the X chromosome. Twelve MAGE family genes have been mapped to the distal region of the long arm of the X chromosome (De Plaen, et al., *Immunogenetics*, 40:360–369, (1994); Oaks et al., *Cancer Research*, 54:1627–1629, (1994)) and MAGE-Xp is located in the Xp21.3 region of the short arm in the region (Muscatelli et al., *Proc. Natl Acad. Sci. USA*, 92:4987–4991, (1995)).

EXAMPLE 10

Identification of Potential HLA Class I-Binding MAGE-C1 Peptides

Searching the MAGE-C1 protein sequence for HLA class I-binding peptides was performed on the Web site: http://blmas.dcrt.nlh.gov/molbio (Parker, K. C., M. A. Bednarek, and J. E. Coligan, "Scheme for ranking potential HLA-A2 binding peptides based on independent binding of individual peptide side-chains", J. Immunol. 152:163 (1994)). Table 3 lists peptides expected to bind to the indicated HLA class I molecules and found more than once in the MAGE-C1 protein.

TABLE 1

MAGE-C1 expression determined by RT-PCR on normal tissue samples.

| Type of tissue | number of samples expressing MAGE-C1/ number of samples assayed |
| --- | --- |
| Bladder | 0/2 |
| Brain | 0/4 |
| Breast | 0/3 |
| Colon | 0/2 |
| Epididymus | 0/1 |
| Kidney | 0/1 |
| Liver | 0/4 |
| Lung | 0/6 |
| Lymphocytes (PBL) | 0/4 |
| Ovary | 0/1 |
| Placenta | 0/1 |
| Prostate | 0/2 |
| Testis | 3/3 |
| Uterus | 0/4 |

TABLE 2

MAGE-C1 expression determined by RT-PCR on tumor samples.

| Tumor type | number of samples expressing MAGE-C1/ number of samples assayed | Percent expressing MAGE-C1 |
| --- | --- | --- |
| Cutaneous melanoma | 48/105 | 46% |
| Primary | 17/46 | 37% |
| Metastatic | 31/59 | 52% |
| Mucosis melanoma | 5/8 | |
| Uveal melanoma | 0/9 | |

TABLE 2-continued

MAGE-C1 expression determined by RT-PCR on tumor samples.

| Tumor type | number of samples expressing MAGE-C1/ number of samples assayed | Percent expressing MAGE-C1 |
| --- | --- | --- |
| Testicular tumors | | |
| Seminoma | 9/9 | 100% |
| Non-seminoma | 0/3 | |
| Neuroblastoma | 1/3 | |
| Bladder transitional-cell carcinoma | 9/51 | 18%. |
| Invasive | 9/37 | 24% |
| Superficial | 0/14 | |
| Breast carcinoma | 6/36 | 16% |
| Lung carcinoma | | |
| NSCLC | 15/95 | 16% |
| SCLC | 0/3 | |
| Sarcoma | 2/17 | 12% |
| Brain tumors | 1/9 | |
| Prostate adenocarcinoma | 2/18 | 11% |
| Head-and-neck squamous-cell carcinoma | 4/42 | 10% |
| Colorectal carcinoma | 0/30 | |
| Leukemia | 0/37 | |
| Myeloma | 0/1 | |
| Renal tumors | 0/8 | |
| Pancreatic tumors | 0/1 | |
| Ovarian tumors | 0/3 | |
| Uterine tumors | 0/9 | |
| Esophageal carcinoma | 0/6 | |
| Mesothelioma | 0/3 | |

TABLE 3

Repeated peptides found in protein MAGE-C1 and expected to bind to HLA class I molecules, as determined by analysis on Web site http://bimas.dcrt.nih.gov/molbio

| HLA Class I molecule | MAGE-C1 peptide | Start position in the MAGE-C1 protein | # of repetitions |
| --- | --- | --- | --- |
| B 60 | FEGFPQSPL | 190, 260, 365, 400, 435, 470, 506 | 7 |
| B 62 | LQIPVSRSF | 198, 268 | 2 |
| B 2705 | LQIPMTSSF | 338, 408 | 2 |
| | ERTQSTFEGF | 254, 289, 324, 464 | 4 |
| B 4403 | GEDSLSPHY | 556, 571, 586 | 3 |
| B 5101 or B5102 | FPSSTSSSL | 817, 834 | 2 |
| | SPPQGEDSL | 551, 567 | 2 |
| | EGFPQSPLQI | 191, 261, 366, 401, 436, 471, 507 | 7 |
| | FPQSPLQIPV | 193, 263, 438, 473 | 4 |
| | EGFAQSPLQI | 226, 296 | 2 |
| | FAQSPLQIPV | 228, 298 | 2 |
| B 5103 | FAQSPLQIPV | 228, 298 | 2 |
| B 5801 | RTQSTFEGF | 255, 290, 325, 265 | 4 |
| Cw 0401 | FPSSTSSSL | 817, 834 | 2 |
| | TFEGFPQSPL | 259, 364, 399, 469, 505 | 5 |
| | SFSSTLLSIF | 205, 275, 345 | 3 |
| | SFPSSTSSSL | 833, 816 | 2 |

We claim:

1. A isolated tumor rejection antigen precursor having an amino acid sequence encoded by a nucleic acid molecule having a nucleotide sequence as set forth in SEQ ID NO:9.

2. The isolated tumor rejection antigen precursor of claim 1 wherein said nucleic acid molecule is a cDNA molecule.

* * * * *

UNITED STATES PATENT AND TRADEMARK OFFICE
CERTIFICATE OF CORRECTION

PATENT NO. : 5,997,872
DATED : Dec. 7, 1999
INVENTOR(S) : Lucas et al.

It is certified that error appears in the above-indentified patent and that said Letters Patent is hereby corrected as shown below:

In column 1, line 52, change "PCT/US92104254" to -- PCT/US92/04254 --.
In column 1, line 63, change "Nos." to -- No. --.
In column 2, line 49, change "Nos." to -- No. --.
In column 3, line 6, delete -- ; --.
In column 5, line 29, change "CL" to -- C1 --.

Signed and Sealed this

Tenth Day of April, 2001

Attest:

NICHOLAS P. GODICI

Attesting Officer       Acting Director of the United States Patent and Trademark Office